US012788270B2

(12) United States Patent
Ayu et al.

(10) Patent No.: US 12,788,270 B2
(45) Date of Patent: Nov. 10, 2026

(54) LUNG HEALTH SENSING THROUGH VOICE ANALYSIS

(71) Applicant: Hill-Rom Services PTE. LTD., Singapore OT (SG)

(72) Inventors: Aaron A. Ayu, Singapore (SG); Helmi Kurniawan, Singapore (SG); Chang Sheng Lee, Singapore (SG); Bobby Gee Han Png, Singapore (SG); Yaolong Lou, Singapore (SG)

(73) Assignee: Hill-Rom Services PTE. LTD., Singapore (SG)

( * ) Notice: Subject to any disclaimer, the term of this patent is extended or adjusted under 35 U.S.C. 154(b) by 348 days.

(21) Appl. No.: 17/464,582

(22) Filed: Sep. 1, 2021

(65) Prior Publication Data

US 2022/0061694 A1 Mar. 3, 2022

Related U.S. Application Data

(60) Provisional application No. 63/073,561, filed on Sep. 2, 2020.

(51) Int. Cl.
*A61B 5/08* (2006.01)
*A61B 5/00* (2006.01)

(52) U.S. Cl.
CPC .......... *A61B 5/0803* (2013.01); *A61B 5/7267* (2013.01); *A61B 5/749* (2013.01)

(58) Field of Classification Search
None
See application file for complete search history.

(56) References Cited

U.S. PATENT DOCUMENTS 5,853,005 A * 12/1998 Scanlon ............... A61B 5/6896 381/166
7,267,652 B2 9/2007 Coyle et al.
(Continued)

FOREIGN PATENT DOCUMENTS

CN 106782616 A 5/2017
CN 108135485 A 6/2018
(Continued)

OTHER PUBLICATIONS

Nathan, et al., "Extraction of Voice Parameters from Continuous Running Speech for Pulmonary Disease Monitoring," 2019 IEEE International Conference on Bioinformatics and Biomedicine (BIBM), 2019, 3 pages.
(Continued)

*Primary Examiner* — Michael R Bloch
(74) *Attorney, Agent, or Firm* — Lee & Hayes, P.C.

(57) ABSTRACT

A patient monitoring system includes a microphone that collects audio data from a patient. The audio data is used to generate audio characteristics for categorization of the audio data and analysis of the audio data to determine a patient health status. The audio characteristics and the patient health status are tracked over time and utilized to monitor a respiratory condition of the patient. The system determines the patient health status based on a comparison of the audio characteristics with a database of audio characteristics associated with recorded health statuses of various patients. The system generates a report of the current patient health status based on the database of audio characteristics and associated health statuses.

20 Claims, 6 Drawing Sheets

(56) References Cited

U.S. PATENT DOCUMENTS

| | | | |
|---|---|---|---|
| 9,070,357 B1 | 6/2015 | Kennedy et al. | |
| 10,201,307 B2 | 2/2019 | Hampton et al. | |
| 10,475,530 B2 | 11/2019 | Harper et al. | |
| 10,515,629 B2 | 12/2019 | Harper | |
| 2011/0054335 A1* | 3/2011 | Zhang | A61B 5/349 600/509 |
| 2015/0216448 A1 | 8/2015 | Lotan et al. | |
| 2018/0177483 A1* | 6/2018 | Ye | A61H 23/004 |
| 2018/0296092 A1 | 10/2018 | Hassan et al. | |
| 2019/0021593 A1* | 1/2019 | Kwak | A61B 7/00 |
| 2019/0080803 A1 | 3/2019 | Lotan et al. | |
| 2019/0200937 A1 | 7/2019 | Mena Benito et al. | |
| 2019/0221317 A1* | 7/2019 | Kempanna | G16H 20/00 |
| 2020/0035261 A1* | 1/2020 | Mitchell | G16H 50/20 |
| 2020/0098384 A1 | 3/2020 | Nematihosseinabadi et al. | |
| 2020/0118583 A1 | 4/2020 | Shallom | |
| 2020/0146623 A1 | 5/2020 | Anushiravani et al. | |
| 2020/0151519 A1 | 5/2020 | Anushiravani et al. | |
| 2021/0134319 A1* | 5/2021 | Vatanparvar | A61B 5/0823 |

FOREIGN PATENT DOCUMENTS

| | | |
|---|---|---|
| KR | 1020180099434 | 9/2019 |
| KR | 1020190113390 B1 | 3/2020 |
| WO | WO2006002338 A2 | 1/2006 |
| WO | WO2014045257 A1 | 3/2014 |
| WO | WO2019/122412 A1 | 6/2019 |
| WO | WO2019190071 A1 | 10/2019 |

OTHER PUBLICATIONS

Nathan, et al., "Extraction of Voice Parameters from Continuous Running Speech for Pulmonary Disease Monitoring," 2019 IEEE International Conference on Bioinformatics and Biomedicine (BIBM), 2019, pp. 859-864.

Extended European Search Report mailed Jan. 26, 2022 for European Patent Application No. 21194350.1. 11 pages.

International Search Report and Written Opinion for PCT Application No. PCT/SG2021/050531, mailed Dec. 9, 2021.

Office Action for Chinese Application No. 202180003130.9, Dated Nov. 30, 2024, 24 pages.

Examination Report for European Application No. 21194350.1, Dated Dec. 10, 2024, 5 pages.

Office Action for Chinese Application No. 202180003130.9, Dated May 24, 2025, 22 pages.

* cited by examiner

LUNG HEALTH SENSING THROUGH VOICE ANALYSIS

CROSS REFERENCE TO RELATED APPLICATIONS

The present application claims priority of U.S. Provisional Patent Application No. 63/073,561, which was filed Sep. 2, 2020 and is incorporated herein by reference in its entirety.

TECHNICAL FIELD

This application is directed to medical equipment, and in particular, to systems and methods associated with determining lung health information, patient recovery status, and/or other parameters.

BACKGROUND

Numerous respiratory diseases and respiratory conditions are associated with symptoms that affect patient airways (e.g., nose, mouth, trachea, bronchi, lungs, etc.). Additionally, and based on the symptoms associated with the respiratory diseases and respiratory conditions, the ability of the patient to speak and breath may be reduced, modified, or otherwise impacted. Further, and based on the symptoms associated with the respiratory diseases and respiratory conditions, audio events that are audible or inaudible to humans may occur as a result of the symptoms that the patient is experiencing. Such diseases may include asthma, chronic obstructive pulmonary disease (COPD), bronchitis, emphysema, lung cancer, cystic fibrosis, pneumonia, and pleural effusion. The symptoms caused by the respiratory diseases and respiratory conditions can include inflammation of the airways, modified and/or reduced breathing capacity, mucus production, coughing events, difficulty breathing, and other symptoms of respiratory illness. Accordingly, a medical practitioner may diagnose a patient based on one or more of the above symptoms, and may provide medical treatment for the respiratory illness(es).

However, while a medical practitioner may observe the above symptoms through examination and testing of the patient, the medical practitioner may only observe the symptoms of the patient while the patient is being actively diagnosed and/or treated within a medical environment. Additionally, monitoring the symptoms of the patient during treatment and recovery is commonly accomplished via either medical practitioner observations and/or utilization of monitoring devices within the medical environment. Such devices typically include physical leads and/or attachments that are coupled to the patient in order to effectively monitor respiratory activity of the patient. Such devices can be cumbersome and difficult for the medical practitioner to use. Such devices can also cause discomfort if the leads or other attachments thereof are coupled to the patient for extended periods of time. Such devices can also be limited in use due to consistent, passive monitoring of a patient involving use of technology and devices that are localized to a medical environment.

The various examples of the present disclosure are directed toward overcoming one or more of the deficiencies noted above.

SUMMARY

In an example of the present disclosure, a system can include a microphone operable to generate audio data from noises originating from a patient and/or an individual. The audio data captured by microphones associated with the system can be generated by human vocal cords, human lungs, human motions, and/or other sources associated with the patient and/or the individual. In particular, speech generation, via the vocal cords of the patient, can be affected by inhalation and exhalation of air into and out of the lungs of the patient. Additionally, the vocal cords and lungs of the patient can be affected, modifying the speech generated by the patient, when the patient is afflicted with a respiratory illness, a respiratory disease and/or a respiratory condition. Voice parameters can be generated by the microphones, associated with the system, based on the speech of the patient as well as other respiratory sounds of the patient. The voice parameters characterize at least pitch, tone, rhythm, volume, and rate of speech associated with the patient. The system can utilize a voice recognition algorithm to analyze the voice parameters associated with the patient to match and compare a current status of the patient to a previous status of the patient and/or an additional status associated with a second patient.

An example system may include memory, one or more processors, and computer-executable instructions stored in the memory and executable by the one or more processors to perform various operation. For instance, the operations may include receiving, from a user device, current audio data associated with a patient and identifying, based at least on the current audio data, at least one of vocal utterances and breathing sequences of the patient. Additionally, the operations may include determining, based on the at least one of the vocal utterances and the breathing sequences, and on at least one of previous vocal utterances associated with the patient and previous breathing sequences associated with the patient, one or more audio events. Further, operations may include determining one or more first audio characteristics associated with the one or more audio events and determining, based at least on the one or more first audio characteristics, a category of audio events associated with the one or more audio events, wherein the category of audio events associated with secondary audio characteristics indicative of a respiratory condition of the patient. Accordingly, a current health status of the patient associated with the respiratory condition may be determined based at least on a comparison between the one or more audio events and the category of audio events.

An example method executed by a patient monitoring system may include causing a microphone to record current audio data from a patient, the current audio data including patient vocal utterances and patient breathing sequences and receiving the current audio data from the microphone. Additionally, the method may include identifying, based at least on previous audio data, current vocal characteristics associated with the patient vocal utterances and current breathing characteristics associated with the patient breathing sequences and training a machine learning algorithm using the previous audio data, previous vocal characteristics associated with the patient, and previous breathing sequences associated with the patient. Further, the method may include determining, using the machine learning algorithm, and based on a comparison of the current vocal characteristics and the previous vocal characteristics, a current health status of the patient.

An additional example patient monitoring system can perform operations that include causing a microphone associated with a user device to collect a first audio recording, wherein the first audio recording includes at least one of a patient speaking or the patient breathing, receiving, from the user device, the first audio recording, determining, based at least on the first audio recording, an audio category associated with the first audio recording, the audio category associated with one or more vocal utterances that share one or more audio characteristics. Additionally, and based at least on the audio category, the operations can include determining a first patient health status, the first patient health status associated with one or more respiratory symptoms of the patient. Further, the operations can comprise causing the microphone associated with the user device to collect a second audio recording, identifying, based at least on the second audio recording, the one or more audio characteristics associated with the first audio recording and the second audio recording, and determining, based at least on the one or more audio characteristics, a second patient health status, wherein the second patient health status indicates one or more health status changes relative to the first patient health status.

BRIEF DESCRIPTION OF THE DRAWINGS

Features of the present disclosure, its nature, and various advantages, may be more apparent upon consideration of the following detailed description, taken in conjunction with the accompanying drawings.

In the figures, the left-most digit(s) of a reference number identifies the figure in which the reference number first appears. The use of the same reference numbers in different figures indicates similar or identical items or features. The drawings are not to scale.

DETAILED DESCRIPTION

Figure 1:
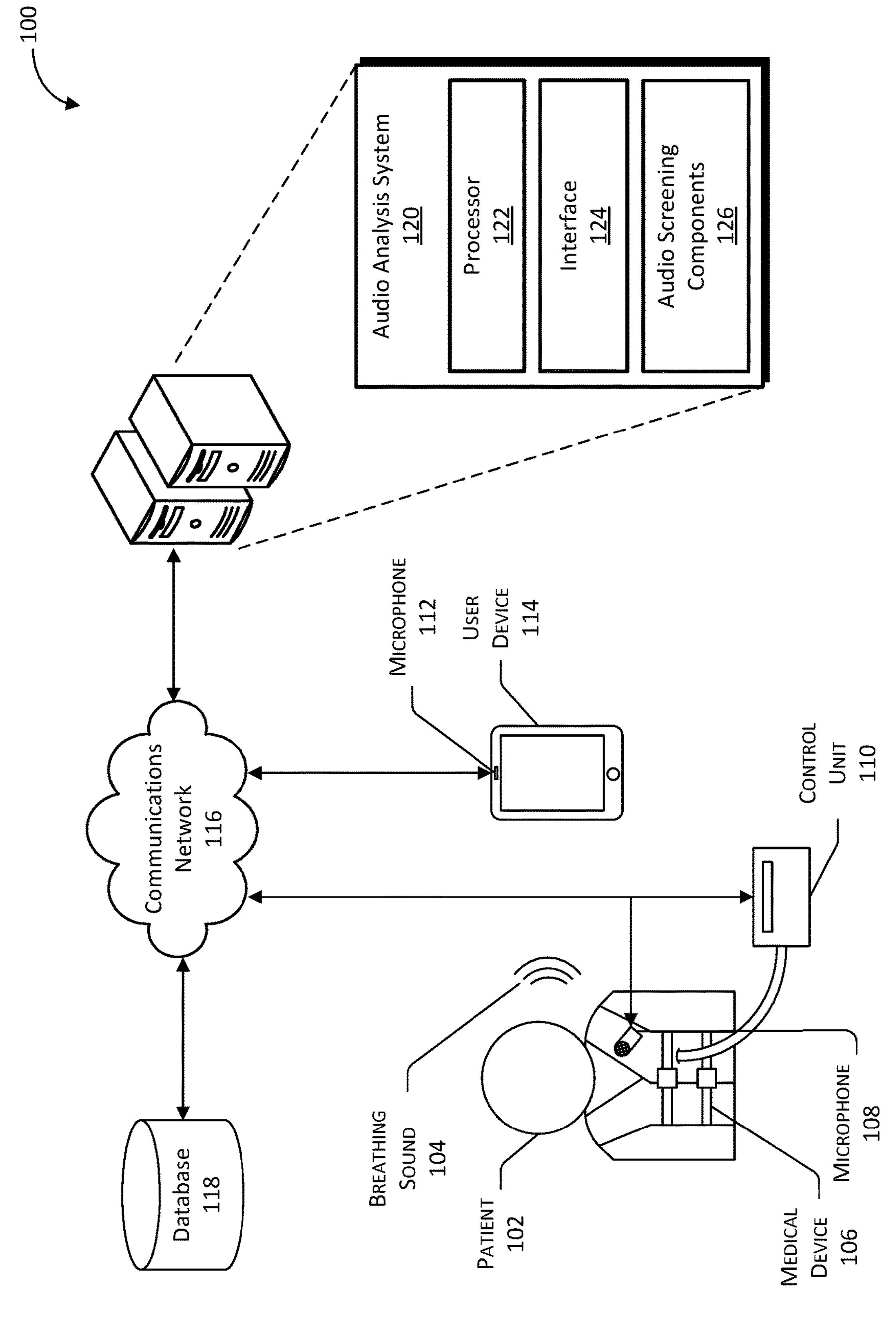
FIG. 1 illustrates an example system of the present disclosure. In some implementations, components of the example system shown in FIG. 1 may be used to monitor a current health status of a patient.

The present disclosure is directed to, in part, a patient monitoring system and corresponding methods. Such an example patient monitoring system may be configured to collect speech data and audio data associated with a patient or an individual, perform analysis on the speech data and audio data, and output the results of the analysis to a user of the device, such as a physician or a physician's assistant. For example, the patient monitoring system may utilize one or more microphones associated with a medical device, a user device, a patient device, or other device that is configured to collect the speech data and the audio data. The system may receive the speech data and the audio data and perform comparative and matching analysis, via a voice recognition algorithm. Moreover, the system may determine, based on the comparative and matching analysis, whether the speech data and the audio data match previous speech data and previous audio data, for the patient, and how the speech data and the audio data compare to the previous speech data and the previous audio data. Accordingly, the system can be utilized to monitor the status of the patient through analysis of various vocal characteristics and additional audio characteristics produced by the patient. In addition, the system may generate a recommendation and/or diagnosis associated with the patient for display to the user of the patient monitoring system. For example, by utilizing standard testing data and/or machine learning techniques, the system may evaluate the measurements determined by the system to provide a recommendation to the user regarding the health of the patient (e.g., whether the patient satisfies one or more thresholds, whether additional monitoring of the patient is to be completed, etc.). As such, the system described herein may provide automated diagnosis recommendations in order to assist the physician or other user of the patient monitoring system.

In any of the examples described herein, the patient monitoring system can be configured to monitor a patient diagnosed with one or more respiratory illnesses. For example, the patient may be diagnosed with asthma, chronic obstructive pulmonary disease (COPD), bronchitis, emphysema, lung cancer, cystic fibrosis, pneumonia, pleural effusion, or other respiratory illnesses. Additionally, the patient monitoring system can be configured to track vocal characteristics that may be modified by the one or more respiratory illnesses that the patient is afflicted with. For example, the patient monitoring system can be configured to determine one or more vocal characteristics from audio data collected from the patient, the one or more vocal characteristics comprising pitch, tone, rhythm, volume, rate of speech, audio events, and other vocal characteristics associated with the patient. Further, the patient monitoring system can be configured to monitor the one or more vocal characteristics associated with the one or more respiratory diseases. The one or more vocal characteristics may be passively collected from the patient (e.g., collected without a triggering incident or phrase) to monitor a recovery or treatment progress associated with the respiratory diseases. For instance, the one or more respiratory illnesses may be associated with one or more symptoms that can be correlated with modified vocal characteristics of the patient. In some examples, asthma can be associated with inflammation of patient airways; COPD can be associated with an inability to exhale normally fully, and/or properly; bronchitis can be associated with excess mucus in the patient airways and a chronic cough; emphysema can be associated with the patient struggling to exhale air from the lungs of the patient; lung cancer can be associated with chronic coughing, changes in the voice of the patient, harsh breathing sounds, and coughing up blood; cystic fibrosis can be associated with chronic coughing, frequent lung infections, mucus pooling in the patient airways, frequent respiratory infections, wheezing, and shortness of breath; pneumonia can be associated with shortness of breath; pleural effusions can be associated with chest discomfort and shortness of breath, and so on. Accordingly, the patient monitoring system can determine, based at least on the one or more vocal characteristics of the patient, whether the patient is responding to treatment, whether the condition of the patient is improving, and what the status of the patient is currently.

Additionally, in any of the examples herein, a patient monitoring system may utilize one or more algorithms, neural networks, machine learning components, and/or other components configured to track one or more vocal characteristics over time. In particular, the patient monitoring system can be configured such that changes in the one or more vocal characteristics can be associated with a status of the patient. Additionally, the patient monitoring can receive an indication of the status of the patient and associated the status of the patient with the one or more vocal characteristics captured at a time associated with the indication. Accordingly, the patient monitoring system can identify, at a second time, that the patient is associated with the status based on the one or more vocal characteristics or that the patient is no longer associated with the status based on the one or more vocal characteristics. Further, the patient monitoring system can be provided with a database of patient status indications, wherein a patient status indication from the databased can be associated with a set of vocal characteristics utilized by the patient monitoring system to determine whether a current patient status matches the patient status indication.

Additional details pertaining to the above-mentioned techniques are described below with reference to FIGS. 1-6. It is to be appreciated that while these figures describe example systems and devices that may utilize the claimed methods, the methods, processes, functions, operations, and/or techniques described herein may apply equally to other devices, systems, and the like.

FIG. 1 illustrates an example system 100, such as a patient monitoring system, according to some implementations. As illustrated in FIG. 1, an example patient monitoring system may be utilized to monitor a current status of a patient 102 based at least on a breathing sound 104 produced by the patient 102. For instance, a medical device 106 may be configured to provide treatment for a respiratory illness, a respiratory injury, and/or one or more other respiratory conditions. In at least some examples, the medical device 106 may be a vest or other device that provides respiratory assistance, a ventilator device, a continuous positive airway pressure (CPAP) device, a drug delivery device, an airway clearance device, and other respiratory devices that may be utilized to treat, monitor, or otherwise assist the patient. As described herein, the medical device 106 may include a microphone 108 or be associated with the microphone 108. Additionally, a control unit 110 may be configured to interface with the microphone 108 such that audio data recorded by the microphone can be transmitted to the control unit 110. Further, the microphone 108 may be mounted, attached, affixed, or otherwise physically connected with the medical device 106.

In some examples, a microphone 112 may be configured to monitor the breathing sound 104 produced by the patient and generate audio data from the breathing sound 104. Additionally, a user device 114 may be comprised of the microphone 112 and configured to receive and/or record the audio data generated by the microphone 112. Further, the user device 114 may be a personal device associated with the patient 102, an additional device associated with the medical device 106, and/or a further device configured to monitor the patient 102. The microphone 112 may be an internal microphone associated with the user device 114 or an external microphone that has been communicatively associated with the user device 114.

It should be understood that, while FIG. 1 depicts the system 100 including a single medical device 106 and a single user device 114, in some additional examples, the system 100 may include any number of local or remote medical devices and/or user device substantially similar to the medical device 106 and the user device 114, configured to operate independently and/or in combination, and configured to communicate via the network 116. In some further examples, the system 100 may include one or more databases 118 and one or more audio analysis systems 120 comprised of one or more processors 122, one or more network interfaces 124, and/or audio screening components 126. The audio screening components 126 may include one or more programs, modules, engines, instructions, algorithms, neural networks, machine learning components, and/or other patient screening components that are executable by the processor(s) 122.

As described herein, the medical device 106, the control unit 110, the user device 114 and/or audio analysis system 120 may be configured to monitor the patient 102 before, during, or after a treatment for the patient 102. For example, monitoring the patient 102 may include collecting breathing sounds 104 from the patient 102 over a period time, analyzing the audio data generated from the breathing sounds 104, determining one or more voice/vocal characteristics from the audio data, tracking variations in the one or more voice/vocal characteristics during the period of time, and determining patient health information from the variations in the one or more voice/vocal characteristics. In particular, the medical device 106, the control unit 110 and/or the user device 114 can be configured to receive audio data, generated from the breathing sounds 104, from at least one of the microphone 108 and/or the microphone 112. Additionally, the medical device 106, the control unit 110, and/or the user device 114 can be configured to locally analyze the audio data to determine the one or more vocal characteristics and track the one or more vocal characteristics over time. Alternatively, or in addition, the medical device 106, the control unit 110, and/or the user device 114 may include wireless and/or wired communication capabilities capable of transmitting the audio data generated from the breathing sounds 104 to other devices associated with the patient monitoring system (i.e., the medical device 106, the control unit 110, the user device 114, and/or the audio analysis system 120). It should be noted that the microphone 108 and/or the microphone 112 may include audio recording components that include a transducer (i.e., a component capable of converting sound or mechanical movement into an electrical signal), a diaphragm for converting the sound into mechanical motion, a signal output (i.e., a port, cable, or other signal carrying component), a microphone housing and/or any other audio devices configured to collect at least the breathing noises 104 and provide a signal that may be recorded as audio data. In some further examples, the microphone 108 and/or the microphone 112 may be a condenser microphone, a radio frequency (RF) condenser microphone, an electret microphone, a dynamic microphone, a ribbon microphone, a piezoelectric microphone, a fiber optic microphone, or other microphone capable of capturing the breathing noises 104. Regardless of the type of microphone utilized by the above devices, a microphone may be selected for use in association with the patient monitoring system based on a capability to perform high-fidelity recording (e.g., a capability to record sounds that are audible and inaudible to human hearing while accurately capturing the audio profile of the audible and inaudible sounds).

In examples, a memory associated with the medical device 106, the control unit 110, the user device 114 and/or audio analysis system 120 may be configured to store and/or access data associated with the patient 102. For example, the patient 102 and/or a user of the patient monitoring system may provide data (referred to herein as "patient data") upon initiating patient monitoring. For instance, when the medical device 106, the control unit 110, the user device 114 and/or audio analysis system 120 are utilized to monitor breathing sounds 104 associated with the patient 102, a patient data file may be created for the audio data generated from the patient and include the patient data. Additionally, the patient 102 may provide, or the user may request, patient data including demographic information, physical characteristics, preferences, and similar information regarding the patient 102. For example, the patient 102 may provide demographic information such as name, age, ethnicity, gender, and the like. The patient 102 may also provide physical characteristic information such as height of the patient 102. In such examples, the user may request the patient data while the patient 102 is being monitored, or before the monitoring has begun. In some examples, the user may be provided with predetermined categories associated with the patient 102, such as predetermined age ranges (e.g., six to twelve months, one to five years old, etc.), and may request the patient data in order to select the appropriate category associated with the patient 102. In other examples, the user may provide a free form input associated with the patient data. In still further examples, an input element may be provided to the patient 102 directly.

In some examples, the medical device 106, the control unit 110, the user device 114 and/or audio analysis system 120 may be configured to generate audio data associated with the patient 102 at the onset of the patient monitoring process. For example, the medical device 106 and/or the user device 114 may include one or more microphones, audio sensors, or other audio capture devices configured to generate audio data over time from the breathing sounds 104 of the patient 102. Alternatively, or in addition, the medical device 106 and/or the user device 114 may include one or more microphones, audio sensors, or other audio capture devices configured to generate additional audio data over time from speech produced by the patient. Further, one or more processors of the medical device 106 and/or the user device 114 may analyze the collected audio data to determine, for example, one or more audio characteristics that include at least one of pitch, tone, rhythm, volume, and rate of speech associated with the patient. Alternatively, or in addition, the medical device 106 and/or the user device 114 may analyze the collected additional audio data to determine one or more voice parameters that include at least one of pitch, tone, rhythm, volume, and rate of speech associated with the patient.

Alternatively, or in addition, the medical device 106, the control unit 110, and/or the user device 114 may be configured to transmit the audio data, the additional audio data, and/or any other collected information to the audio analysis system 120, via the network 116, for analysis. In any such examples, the audio analysis system 120 may store such information in the audio screening components 126 and/or in an external database 118. For example, the database 118 may comprise memory or computer-readable media substantially similar to and/or the same as the computer-readable media associated with the audio screening components 126. The database 118 may be accessible by the audio analysis system 120, and/or by the medical device 106, the microphone 108, the control unit 110, and/or the user device 114, via the network 116. In any such examples, the database 118 may be configured to store patient data in association with a patient ID (e.g., a name, social security number, an alphanumeric code, etc.) or other unique patient identifier. When the patient 102 and/or the user enters the patient ID, the audio screening components 126 may access or receive patient data stored in association with the patient ID.

As used herein, the network 116 is typically any type of wireless network or other communication network known in the art. Examples of network 116 include the Internet, an intranet, a wide area network (WAN), a local area network (LAN), and a virtual private network (VPN), cellular network connections and connections made using protocols such as 802.11a, b, g, n and/or ac.

In some examples, the medical device 106, the microphone 108, the control until 110, and/or the user device 114 can include a microprocessor or a control unit configured to execute instructions stored in computer-readable media to perform various operations and methods. For example, the medical device 106 and/or the control until 110 may comprise one or more processors and/or other hardware and/or software components configured to operably control the microphone 108. Similarly, the user device 114, may comprise one or more processors and/or other hardware and/or software components configured to operably control the microphone 112. Additionally, the one or more processors of the medical device 106, the microphone 108, the control until 110, and/or the user device 114 may be configured to provide a user interface, voice recognition algorithms, and other components of the patient monitoring system. In some additional examples, the medical device 106, the microphone 108, the control until 110, the user device 114, and/or the audio analysis system 120 may include a single processing unit (e.g., a single processor) or a number of processing units (e.g., multiple processors), and can include single or multiple computing units and/or multiple processing cores. The processor(s) 122 of the medical device 106, the microphone 108, the control until 110, the user device 114, and/or the audio analysis system 120 can be implemented as one or more microprocessors, microcomputers, microcontrollers, digital signal processors, central processing units, state machines, logic circuitries, and/or any devices that manipulate signals based on operational instructions. For example, the processor(s) 122 of the medical device 106, the microphone 108, the control until 110, the user device 114, and/or the audio analysis system 120 can be one or more hardware processors and/or logic circuits of any suitable type specifically programmed or configured to execute the algorithms, operations, and methods described herein. The processor(s) 122 of the medical device 106, the microphone 108, the control until 110, the user device 114, and/or the audio analysis system 120 can be configured to fetch and execute computer-readable instructions stored in the audio screening components 126, which can program the processor(s) 122 to perform the functions described herein. Additionally, or alternatively, the processor(s) 122 of the medical device 106, the microphone 108, the control until 110, the user device 114, and/or the audio analysis system 120 can be configured to fetch and execute computer-readable instructions stored in computer-readable media and/or other memory of/local to the various devices.

As described herein, a processor, such as processor(s) 122, can be a single processing unit or a number of processing units, and can include single or multiple computing units or multiple processing cores. The processor(s) 122 can be implemented as one or more microprocessors, microcomputers, microcontrollers, digital signal processors, central processing units, state machines, logic circuitries, and/or any devices that manipulate signals based on operational instructions. For example, the processor(s) 122 can be one or more hardware processors and/or logic circuits of any suitable type specifically programmed or configured to execute the algorithms and processes described herein. The processor(s) 122 can be configured to send, receive, and transmit communications via a network interface. Additionally, the processor(s) 122 can be configured to fetch and execute computer-readable instructions stored in the computer-readable media of the audio screening components 126, which can program the processor(s) 122 to perform the functions described herein.

A network interface(s) associated with the medical device 106, the microphone 108, the control until 110, the user device 114, and/or the audio analysis system 120 may enable wired and/or wireless communications between the components and/or devices shown in patient monitoring system 100 and/or with one or more other remote systems, as well as other networked devices. For instance, at least some of the network interface(s) may include a personal area network component to enable communications over one or more short-range wireless communication channels. Furthermore, at least some of the network interface(s) may include a wide area network component to enable communication over a wide area network. Such network interface(s) may enable, for example, communication between the medical device 106, the microphone 108, the control until 110, the user device 114, and/or the audio analysis system 120 and/or other components of the system 100, via the network 116.

The audio screening components 126 may include volatile and nonvolatile memory and/or removable and non-removable media implemented in any type of technology for storage of information, such as computer-readable instructions, data structures, program modules, or other data. Memory can include, but is not limited to, RAM, ROM, EEPROM, flash memory or other memory technology, optical storage, solid state storage, magnetic tape, magnetic disk storage, RAID storage systems, storage arrays, network attached storage, storage area networks, cloud storage, or any other medium that can be used to store the desired information and that can be accessed by a computing device. The patient screening components 126 can include various types of computer-readable storage media and/or can be a tangible non-transitory media to the extent that when mentioned, non-transitory computer-readable media exclude media such as energy, carrier signals, electromagnetic waves, and signals per se.

The audio screening components 126 can include any number of functional components that are executable by the processor(s) 122. In many implementations, these functional components comprise instructions or programs that are executable by the processor(s) 122 and that, when executed, specifically configure the one or more processor(s) 122 to perform the actions associated with monitoring the health status of the patient.

Although not illustrated in FIG. 1, in some examples the audio screening components 126 may include computer-readable media configured to store an audio data analysis component. In such examples, the audio data analysis component may be configured to receive, access, and/or analyze audio data collected and/or detected by the medical device 106, the microphone 108, the control until 110, and/or the user device 114 during a patient monitoring procedure. For example, the audio data analysis component may be configured to receive, via the network 116, audio data. The audio data may be generated from breathing sounds 104 and/or speech produced by the patient by the various devices and/or microphones discussed above during patient monitoring procedures. The audio data analysis component may analyze the audio data to determine one or more vocal characteristics, breathing characteristics, and/or audio characteristics associated with the patient 102, such as pitch, tone, rhythm, volume, and rate of speech associated with the patient 102.

Further, although not illustrated in FIG. 1, the audio screening components 126 may also include computer-readable media configured to store a diagnostic data component. The diagnostic data component may be configured to receive, access, and/or analyze diagnostic data associated with the patient 102 and the health status associated with the patient. For example, in such embodiments, the diagnostic data component may be configured to access or receive data from one or more additional databases (e.g., the database 118, a third-party database, etc.) storing testing data, medical practitioner evaluations, previous measurement data, and/or a range of values indicating various thresholds or ranges within which audio characteristics and vocal characteristics, determined from audio data associated with the patient 102, should fall. Such thresholds or ranges may be associated with an initial health status of the patient 102, a targeted health status of the patient 102 and/or one or more additional patients, and/or a current health status of the patient 102 relative to a previous health status of the patient 102. For example, individual and/or standardized diagnostic data may be accessed or received by the diagnostic data component and may be utilized for comparison against the audio data/audio data characteristics generated and stored by the audio data analysis component described above. For instance, the diagnostic data associated with the patient 102 may include standard measurements (i.e., pitch, tone, rhythm, volume, and rate of speech associated with the patient 102) obtained when the patient 102 was evaluated as healthy and/or at the target health status. Additionally, or alternatively, the diagnostic data associated with the patient 102 may include standard measurements (i.e., pitch, tone, rhythm, volume, and rate of speech associated with the patient 102) obtained when the patient 102 was evaluated as afflicted with a respiratory illness and/or condition (i.e., asthma, COPD, bronchitis, emphysema, lung cancer, cystic fibrosis, pneumonia, and pleural effusion) and determined to have an initial health status associated with the evaluation. Accordingly, the standard measurements may identify a threshold range of audio characteristic and/or vocal characteristic values that current audio characteristics and/or vocal characteristics should achieve (i.e., standard measurements associated with the target health status) and/or improve from (e.g., standard measurements associated with an initial health status. Further, the standard measurements can integrate diagnostic data from other patients to determine whether the patient 102 is properly recovering from the initial health status, whether the patient 102 is progressing towards the targeted health status, whether the health of the patient 102 has fallen below the targeted health status, and/or other assistance in monitoring the patient 102.

Figure 2:
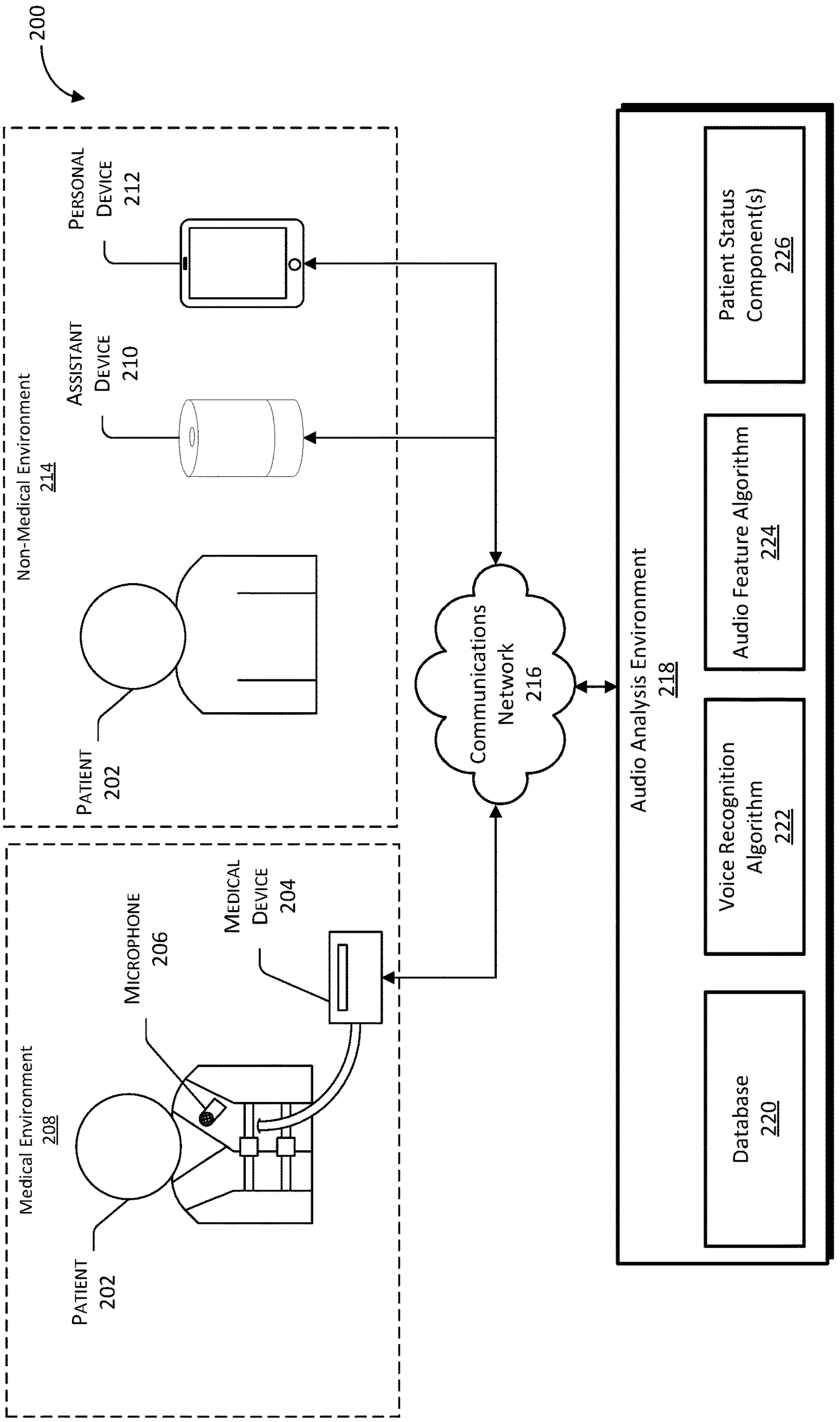
FIG. 2 illustrates another example system of the present disclosure.

FIG. 2 illustrates an additional example system 200 of the present disclosure. In some examples, the system 200 may include one or more of the same components included in the system 100. In some additional examples, the system 200 can include different components that provide similar functions to the components included in the system 100. As shown in FIG. 2, the system 200 can be utilized to determine monitor a patient 202 within a medical environment 208 and a non-medical environment 214, over a period of time. Within the medical environment 208, the patient 202 may be associated with a medical device 204 and a microphone 206. Within the non-medical environment 214, the patient 202 may be monitored via an assistant device 210 and/or a personal device 212. It should be noted that the assistant device 210 and the personal device 212 may comprise one or more additional microphones that are the same or different as the microphone 206. Additionally, the medical device 206, the assistant device 210, and the personal device 212 can transmit audio data, via a communication network 216, to an audio analysis environment 218. The audio analysis environment 218 can comprise a database 220 configured to store audio data generated from the patient 202, a voice recognition algorithm 222, an audio feature algorithm 224, and a patient status component 226.

In the example system 200 of FIG. 2, and as noted with respect to FIG. 1, a microphone 206 associated with a medical device 204 can monitor a patient 202 during a treatment. For instance, the microphone 206 can collected and record one or more vocal utterances, breathing samples, audio events, and/or other utterances produced by the patient 202. The one or more vocal utterances may comprise a conversation, a requested phrase, and/or other sounds produced at least in part by vocal cords of the patient 202. Similarly, the one or more breathing samples may comprise extended periods of patient breathing, breathing patterns during patient sleep cycles, breathing patterns during treatment of the patient 202, and/or other sounds produced at least in part by the inhalation and exhalation of air from the lungs of the patient 202. Further, the one or more audio events may comprise groans, whines, sharp inhalation/exhalation of air, gasps, choking events, and other audio events that may indicate the status of the airways of the patient 202.

In the example system of FIG. 2, the microphone 206 can by utilized to collect audio data from the patient 202 within the medical environment 208. Additionally, the audio data collected by the microphone 206 may be transmitted, via the communication network 216, to the audio analysis environment 218. Further, the audio data may be stored in a database 220 in association with contextual information of the audio data. The contextual data may include device information, time information, medical device associations, location data, medical data, and other information associated with the patient 202 or the medical environment 208. The audio analysis environment 218 may be configured to determine, from the audio data collected within the medical environment 208, one or more audio characteristics from the audio data. For instance, the audio characteristics can include vocal characteristics associated with the one or more vocal utterances, wherein the vocal characteristics can include a pitch, tone, rhythm, volume and/or rate of speech as data points. Additionally, the vocal characteristics can be determined by the voice recognition algorithm 222 from the audio data obtained from the patient 202. Further, the patient status component 226 can be configured to determine, from the vocal characteristics, an initial health status for the patient 202 within the medical environment 208.

In the example system of FIG. 2, the voice recognition algorithm 222 may be configured to utilize digital signal processing and one or more audio filters to break down an audio sample into audio characteristics (e.g., pitch, rhythm, energy spectrum, volume, etc.). For instance, the voice recognition algorithm 222 may utilize the audio characteristics determined from the audio sample as identifiers for the patient 202 associated with the audio sample. Additionally, the voice recognition algorithm 222 can compare the audio characteristics and/or identifiers from the audio sample against a pre-defined library of healthy patient audio characteristics and unhealth patient audio characteristics. Alternatively, or in addition, the voice recognition algorithm 222 can compare the audio characteristics and/or identifiers from the audio sample against a collation of historical patient audio samples associated with the patient 202. The pre-defined library of audio characteristics associated with healthy and/or sick patients may include a large number of patient audio samples collected from healthy/sick patients. Similarly, the collation of historical patient audio samples may include a large number of historical audio samples and historical audio characteristics obtained from the patient 202. Further, the voice recognition algorithm 222 may utilized the pre-defined library and/or the collation of historical patient audio characteristics to compare and/or match the audio characteristics of the audio sample with the patient audio samples of the pre-defined library and/or the collation of historical patient audio characteristics and historical audio data. The pre-defined library and/or the collation of historical patient audio characteristics can be stored in the database 220. Accordingly, the collation of historical patient audio data and the pre-defined library can be utilized to identify patterns and features within the audio data collected from the patient 202 that are associated with a voice of the patient 202, audio characteristics associated with the voice of the patient 202, and other audio information associated with the voice of the patient 202.

In at least one example system, the voice recognition algorithm 222 may be configured to receive audio data from the patient 202 and determine whether the audio data includes one or more vocal utterances. For instance, the voice recognition algorithm 222 can be configured to analyze the audio data and identify audio patterns that are associated with human speech, wherein the audio patterns can include phonemes and/or patterned variations in the vocal characteristics (e.g., pitch, tone, rhythm, volume and/or rate of speech) produced by the patient 202. Additionally, the voice recognition algorithm 222 can be configured to utilize neural network algorithms and machine learning algorithms to identify the audio patterns within the audio data and associate them with the patient 202 within the database 220. Accordingly, the voice recognition algorithm 222 can be configured to parse through the audio data recorded by the microphone 206 and determine whether the patient 202 is speaking. Further, upon determining that the patient 202 is speaking, the voice recognition algorithm 222 can be configured to identify individual phonemes from the vocal utterances of the patient 202, wherein the phonemes represent individual components of human speech that may be combined to for words and other vocal utterances associated with human speech and communication. Alternatively, or in addition, the voice recognition algorithm 222 may be configured to recognize patterned variations in the vocal characteristics, of the patient 202, identified within the audio data.

For example, the voice recognition algorithm 222 may utilize machine learning algorithms, neural networks, artificial intelligence (AI), and/or other techniques to recognize patterns that are associated with voice samples and/or voice patterns in the audio data captured, by the microphone 206, from the patient 202. For instance, the voice recognition algorithm 222 may be configured to determine vocal characteristics from audio characteristics of the audio data. Additionally, the voice recognition algorithm 222 may be trained, based on the pre-defined library and/or the collation of historical patient audio characteristics, to identify and/or recognize vocal patterns/vocal characteristics within audio data. Upon identifying and/or receiving audio characteristics, such as from the audio feature algorithm 224 (e.g., receiving only audio data that has been identified as associated with a voice of the patient 202), the voice recognition algorithm 222 may determine whether the audio characteristics of the audio data match audio samples stored by the pre-defined library and/or the collation of historical patient audio characteristics. Alternatively, or in addition, the voice recognition algorithm 222 may be configured to identify and/or recognize audio characteristics associated with the audio data through analysis of a spectrogram associated with the audio data. Further, the voice recognition algorithm 222 can be configured to record, based on matching the audio samples of the audio data with the pre-defined library and/or the collation of historical patient audio characteristics, vocal characteristics (e.g., pitch, tone, vocal clarity, rhythm of speech, etc.) associated with the human speech generated by the patient 202.

In at least one additional example system, the audio feature algorithm 224 may be configured to receive audio data from the patient 202 and determine whether the audio data includes audio events and/or breathing samples. For instance, the audio feature algorithm 224 can be configured to analyze the audio data and identify audio patterns that are associated with breathing patterns and audio events associated with the patient 202. In particular, the audio feature algorithm can be configured to identify audio events such as groans, whines, sharp inhalation/exhalation of air, gasps, and choking events. Audio events can be identified and recorded in the database, flagging potential indicators of the health status of the patient. Additionally, or alternatively, the audio feature algorithm 224 can be configured to identify breathing patterns and audio characteristics associated with the breathing of the patient 202. Further, the audio characteristics of the breathing of the patient 202 can include a pitch, tone, rhythm, volume and/or rate of breathing for the patient 202. Similarly, the audio feature algorithm 224 can be configured to identify one or more breathing patterns that are associated with the initial health status of the patient 202 within the medical environment 208.

For example, the audio feature algorithm 224 may analyze the audio data captured by the microphone 206 or other devices associated with the system 200. The audio data may be captured substantially continuously and/or passively (e.g., continuous collection of audio data independent of an initiation signal, continuous collection of audio data while the system 200 has power, etc.) from an environment and/or from the patient 202. It should be noted that the audio data can also be collected periodically, aperiodically, in response to an indication, and/or based on other indicators that audio data is to be collected from the patient 202. The microphone 206 may provide the audio data to the audio feature algorithm 224 that includes decibel data, energy data, a spectrograph, and/or other representation of audio data. The audio feature algorithm 224 may execute multiple stages of analysis (e.g., preprocessing, analysis, post-processing, etc.). An initial stage (e.g., preprocessing) of the audio feature algorithm 224 may include receiving the audio data from the microphone 206 and quantizing, sampling, and filtering the audio data to remove noise from the decibel data, the energy data, the spectrograph, and the other representations of the audio data. Additionally, the initial stage of the audio feature algorithm can utilize one or more additional microphones that are associated with the system 200. Further, audio data from the microphone 206 and the additional microphones may be merged and normalized to further improve the quality of the audio data analyzed by the audio feature algorithm 224.

In some examples of the audio feature algorithm 224, the audio feature algorithm 224 may utilize signal processing techniques and natural language processing to classify portions of the audio data as "word" audio characteristics (e.g., human speech) and "non-word" audio characteristics (e.g., groans, whines, etc.). For example, natural language processing can prioritize the identification of common phonemes and audio data patterns that are associated with the most common words and sounds produced by human voice. The identified high priority audio patterns can be utilized to identify "word" audio data that is associated with the word audio characteristics. Similar to the above voice recognition algorithm 222, the audio feature algorithm 224 (or the voice recognition algorithm 222) can utilize stored audio samples of the common phonemes and audio data patterns to train natural language processing algorithms to identify the high priority audio patterns for the identification of word audio data and word audio characteristics extracted from the word audio data. Accordingly, the audio feature algorithm 224 can classify audio data having a comparatively high concentration of the high priority/common audio patterns as word audio data having word audio characteristics.

In some examples of the audio feature algorithm 224, the non-word audio characteristics can be further analyzed to detect breathing patterns and instances of pain noises. For instance, the breathing patterns can be identified from the non-word audio characteristics based on the identification of periodic and/or regular audio characteristics within the non-word audio data. Additionally, the identified breathing patterns can be analyzed to obtain breathing parameters such as peak position of inhalation and exhalation, amplitude of noises made during breathing, duration of inhalation and exhalation, and other breath characteristics that can be utilized to identify disorders and/or diseases of the respiratory system. Further, monitoring the rate of breathing and other indicators detected from the breathing pattern can provide additional indicators of respiratory diseases and/or conditions. In comparison, instances of pain noises (e.g., groans, whines, gasps, grunts, etc.) within the non-word audio characteristics can be identified based on aperiodic, independent, and/or isolated audio characteristics within the non-word audio data. In the final stage of the audio feature algorithm 224, the various word audio characteristics, non-word audio characteristics, breathing patterns, instances of pain noises, and other detected audio features can be stored for further analysis and usage in the system (e.g., the voice recognition algorithm 222 can utilize the word audio characteristics).

In some additional examples of the audio feature algorithm 224, the non-word audio characteristics and/or the word audio characteristics can be utilized to create sound filters to remove and/or reduce audio signals of various audio features from with the audio data. For instance, the audio data waveform can include a periodic audio features that are determined to be associated with breathing patterns of the patient 202. Additionally, the audio data can include audio noise and/or extraneous audio features that are undesirable inclusions in the audio data. Accordingly, a preliminary analysis of the audio data can reveal audio frequencies that are not related or are minimally related to the audio data of interest (e.g., the breathing pattern). Further, an audio filter can be created based on the preliminary analysis to remove the audio frequencies that are unrelated and/or minimally related to the audio data of interest. For example, the preliminary analysis can determine that breathing patterns are primarily associated with audio features within the frequency range of 150 Hz to 1000 Hz. Accordingly, a sound filter can be generated to remove audio features outside of the 150 Hz to 1000 Hz range and reduce the amount of noise and/or extraneous audio data within the audio data being analyzed by the audio feature algorithm 224.

In some further examples of the audio feature algorithm 224, the audio feature algorithm 224 may be configured to identify variations in the standard audio profile of an audio feature. For example, a cough can be identified based on an initial phase (e.g., explosive phase) that is associated with high frequency, high amplitude audio data, a intermediate phase of high frequency, low amplitude audio data, and a voiced phase with intermediate frequency and intermediate amplitude. Additionally, the audio features (e.g., the cough) can be associated with a duration. However, the three phases of the cough associated with the patient 202 can be modified based on one or more symptoms, conditions, and/or diseases associated with the patient. Increased or decreased amplitude, frequency, and duration during each of the three phase can be associated with symptoms of respiratory conditions/diseases. Such modifications to the audio data of the patient 202 may provide indications of narrowed airways, obstructions, widened airways, scarred lungs, restricted lung capacity, fluid filled lungs, and other symptoms of respiratory diseases and/or conditions.

In at least one further example system, the patient status component 226 may be configured to retrieve audio data from the medical device 204 and/or the microphone 206 to determine an initial patient status for the patient 202. In particular, the patient status component 226 can be configured to determining an initial health status for the patient 202 based at least on the contextual data stored in the database 220. For example, the patient status component 226 can determine the initial health status for the patient 202 based at least on a health evaluation of provided by a medical practitioner, an indication provided by the patient 202, or health information associated with other patients. Alternatively, or in addition, the patient status component can determine a range of patient health statuses, wherein the range of patient health statuses may include an optimal health status (e.g., a health status where the patient is not afflicted with a respiratory illness or experience negative symptoms associated with a respiratory condition), a targeted health status (e.g., a health status where the patient is experiencing minimal negative effects due to a respiratory illness and/or respiratory condition), an initial health status (e.g., a health status that indicates respiratory condition before treatment of a respiratory illness and/or respiratory condition), a threshold health status (e.g., a health status that indicates a respiratory condition that can cause further action to be taken), and/or other health statuses that represent patient conditions that are to be reported and/or flagged to be addressed in the future. The initial health status can be determined before the medical device 204 provides treatment to the patient 202 within the medical environment 208 and can be associated with one or more vocal utterances, breathing patterns, and/or audio events recorded by the microphone 206. Similarly, an additional health status can be determined after the medical device 204 provides treatment to the patient 202 within the medical environment 208 and can be associated with one or more additional vocal utterances, additional breathing patterns, and/or additional audio events recorded by the microphone 206. Further health statuses can be established by the patient status component based on an indication provided to the audio analysis system by a health practitioner, the patient 202, the medical device 204, or other system associated with the patient monitoring system.

In the example system of FIG. 2, the system 200 one or more microphones associated with an assistant device 210, a personal device 212, and/or other devices can be configured to collect audio data from the patient 202 in a non-medical environment 214 (e.g., at home, in a workplace, in public, in telemedicine etc.). For instance, the system 200 can be configured to monitor a health status of the patient 202 in the non-medical environment 214. In particular, one or more microphones associated with at least one of the assistant device 210 and/or the personal device 212. It should be noted that the microphones can be comprised of similar components as those described with respect to FIG. 1. Additionally, the assistant device 210 and/or the personal device 212 can operate in coordination and/or independently to collect audio data from the patient 202, within the non-medical environment 214, and transmit the audio data to the audio analysis environment 218. Further, the audio data may be stored in a database 220 in association with contextual information of the audio data. The contextual data from the non-medical environment 214 may include device information, time information, location data, and other information associated with the patient 202 or the non-medical environment 214. The audio analysis environment 218 may be configured to determine, from the audio data collected within the non-medical environment 214, one or more audio characteristics from the audio data. For instance, the audio analysis environment 218 may be configured to determine, from the audio data produced by the patient 202, one or more vocal utterances, breathing samples, audio events, and/or other utterances. It should be noted that the audio characteristics of the audio data may be determined in a manner similar to that discussed above for audio data captured in the medical environment 208.

In an example system of FIG. 2, the communication network 216 may be configured to enable persistent monitoring of the patient within the medical environment 208 and the non-medical environment 214. Additionally, the audio analysis environment 218 may be configured to monitor the patient 202 in a substantially continuous manner, independent of the patient 202 moving between the medical environment 208, the non-medical environment 214, and into/out of range of the various devices associated with the system 200. Further, the audio analysis environment 218 may be configured to determine whether incoming audio data from the medical device 204, the assistant device 210, the personal device 212, and/or additional devices matches any of the recorded health statuses stored in the database 220. For instance, the database 220 may comprise one or more health status thresholds, recorded patient health statuses, and/or associations between audio characteristics and the health status of the patient 202. Additionally, upon determining that the audio data received by the audio analysis environment 218 satisfies one or more health status thresholds and/or matches one or more recorded health statuses, the audio analysis environment 218 may be configured to transmit an indication of the health status threshold(s) being satisfied and/or the recorded health status(es) being matched by the audio data.

In some examples, the audio analysis environment 218 may receive audio data from the medical device 204, the microphone 206, the assistant device 210, the personal device 212, and/or other devices associated with the system 200 via the communication network 216. Additionally, the audio analysis environment 218 may perform comparative analysis and matching analysis between the audio data and patient health status data stored in database 220 (e.g., the patient health status thresholds, the recorded patient health statuses, the patient health status data, etc.). For example, the database 220 can be populated with an initial health status, a target health status, an optimal health status, and/or other health statuses associated with the patient and determined from audio data in a manner similar to that discussed above. It should be noted that while the above discussion related to audio data collected from the patient within a medical environment 208, the audio analysis environment may determine the patient health statuses based at least in part on audio data collected in the non-medical environment 214. Additionally, the patient status component 226 can determine a current health status of the patient 202 through comparative and matching analysis between the current audio data received from the devices associated with the system 200 and previous audio data associated with the patient health statuses.

In some additional examples, the audio analysis environment 218 may determine a current health status for the patient 202 based at least on current audio data received from one or more devices associated with the system 200. As noted above, the patient status component 226 can be configured to identify, from the current audio data, a current health status for the patient 202 determine whether a notification is to be transmitted to the patient 202 and/or a medical practitioner. For instance, the patient status component 226 can compare audio characteristics from the current audio with audio characteristics from previous audio data associated with patient health status data stored in database 220. Additionally, the patient status component 226 can determine that the current audio characteristics substantially match the past audio characteristics stored by the database 220. Further, or alternatively, the patient status component 226 can determine that the current audio characteristics satisfy one or more audio characteristic thresholds associated with the patient health data stored by the database 220. It should be noted that the patient status component 226 can be configured to utilize machine learning algorithms and/or neural network technique to form categories of audio characteristic values that are associated with various respiratory illnesses and/or respiratory conditions. In addition, the patient status component 226 may determine, from the previous audio characteristics, audio characteristic value ranges and thresholds that are associated with symptoms of the respiratory illnesses and/or respiratory conditions. Accordingly, the patient status component 226 can be configured to determine, base at least on the current audio characteristics, a current health status for the patient 202 and/or provide an indication of one or more respiratory illness and/or respiratory conditions that the patient 202 is currently experiencing.

In the example system of FIG. 2, communication interfaces may be configured to provide data connections and network communications for the medical device 204, the assistant device 210, the personal device 212, the audio analysis device 218, and other device associated with the system 200 via the communication network 116 described with respect to FIG. 1. For instance, the communication network 216 may enable the various devices to connect with external databases (e.g., the database 118) to receive, access, and/or send audio data using wireless connections. Wireless connections can include cellular network connections and connections made using protocols such as 802.11a, b, g, and/or ac. In other examples, a wireless connection can be accomplished directly between the audio analysis environment 218 and an external display using one or more wired or wireless protocols, such as Bluetooth, Wi-Fi Direct, radio-frequency identification (RFID), infrared signals, and/or Zigbee. Other configurations are possible. The communication of data to an external database 118 or an external system can enable report printing or further assessment of the audio data and/or the health status of the patient 202. For example, collected data and analysis results may be wirelessly transmitted and stored in a remote database accessible by authorized medical professionals.

Figure 3:
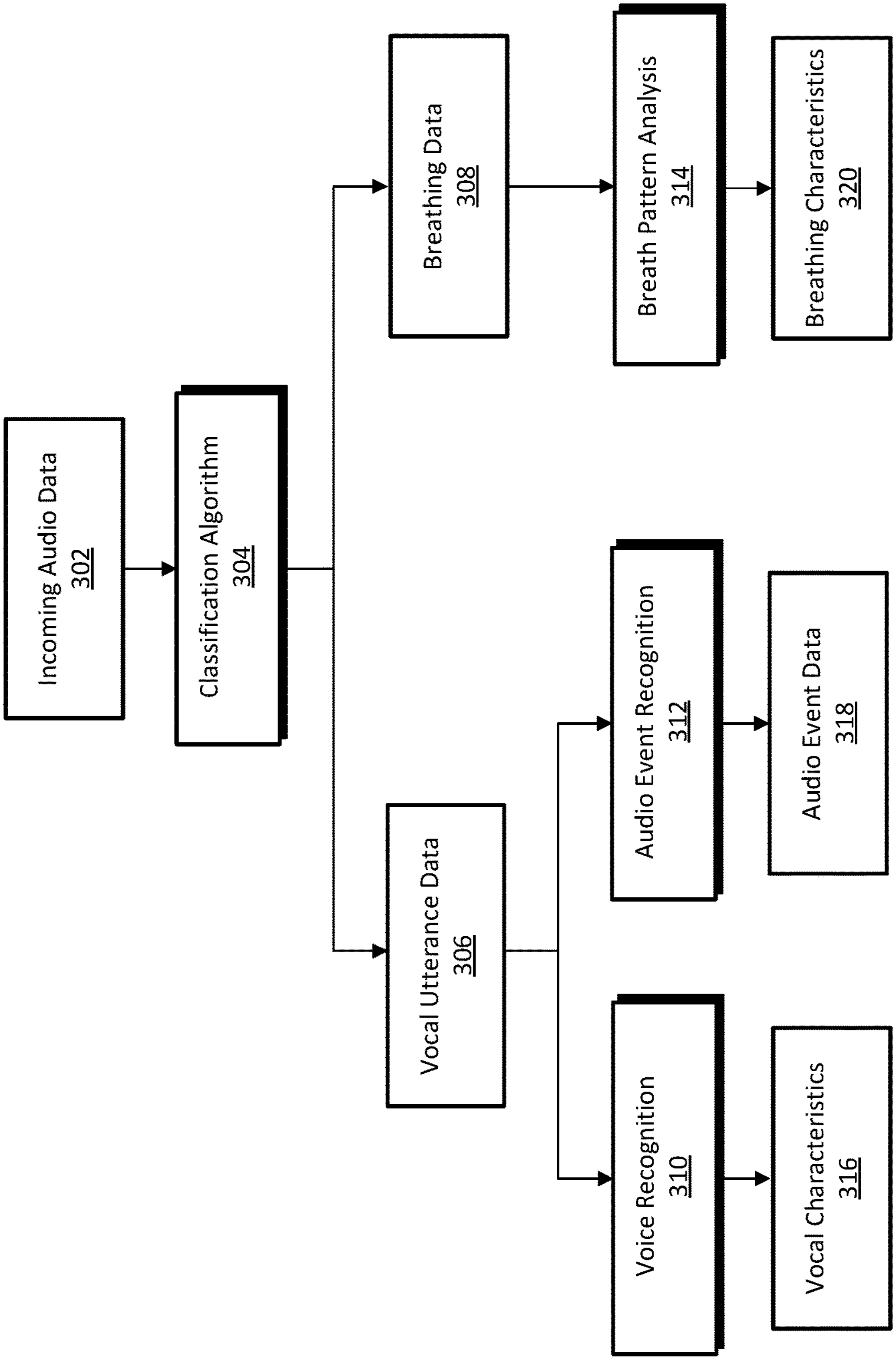
FIG. 3 illustrates a data processing workflow of the present disclosure. In some implementations, the example systems illustrated by FIG. 1 and FIG. 2 may utilize a series of algorithms configured to identify and classify patient data from incoming audio data.

FIG. 3 illustrates an example data processing workflow of the present disclosure. Though not depicted in FIG. 3, in some examples, the workflow may be executed by the example system 100 and/or the example system 200. In some additional examples of FIG. 3, the workflow may be initiated when incoming audio data 302 is received by an example system. Additionally, upon receiving the incoming audio data 302, a classification algorithm 304 may be called, activated, or otherwise initiated to analyze the incoming audio data 302 and identify relevant portions of the incoming audio data 302. For example, the classification algorithm may be configured and/or trained to distinguish between vocal utterances 306, breathing data 308, and/or other audio data included in the incoming audio data 302. Upon parsing the incoming audio data 302 and classifying the relevant portions as vocal utterances 306, breathing data 308, and other audio data types, the example system can activate additional algorithms to further analyze the data. For instance, a voice recognition algorithm 310 and/or an audio event recognition algorithm 312 may be configured to receive the vocal utterance data 306 and identify vocal characteristics 316 and/or audio event data 318 that may be utilized to identify and/or monitor a patient health status. Similarly, breath pattern analysis 314 may be performed to identify breathing characteristics 320 that may be utilized to identify and/or monitor a patient health status.

In some examples of FIG. 3, the incoming audio data 302 may be unprocessed and/or raw audio data collected from a patient and/or an environment that the patient is located within. The incoming audio data 302 may include patient speech, patient breathing, and other audio events associated with the patient. However, the incoming audio may also include other individuals speaking and breathing, ambient sounds (e.g., objects moving within the environment, other individuals walking, electronic audio sources, etc.), and other audio data that is not relevant to the health status of the patient.

In some examples of FIG. 3, a classification algorithm 304 may be utilized to identify vocal utterances 306 and breathing data 308 from the incoming audio data 302. For example, the classification algorithm 304 may be configured to utilize machine learning techniques and neural networks to parse the incoming audio data 302 to identify relevant vocal utterances and breathing data. In particular, a database associated with the example system can comprise a plurality of recordings that sufficiently comprise the entirety of the phonemes produced by a patient while speaking. Additionally, or alternatively, the database can comprise an additional plurality of recordings that sufficiently represent the vocal qualities utilized by the patient during speech. Further, or alternatively, the database can comprise vocal recordings associated with a plurality of individuals, wherein the vocal recordings can be utilized to identify spoken audio data within the incoming audio data 302. Accordingly, the classification algorithm 304 can comprise a machine learning algorithm and/or a neural network that has been trained to recognize the phonemes, vocal qualities associated with the patient, and/or human speech within the incoming audio data 302.

In some additional examples, and similar to above, the database may further comprise data representing breathing patterns of the patient and/or other individuals. The breathing patterns of the database may include passive breathing of the patient and/or other individuals, breathing patterns during speech for the patient and/or other individual, and other breathing patterns. Accordingly, the classification algorithm can comprise a machine learning algorithm and/or a neural network that has been trained to identify inhalations and exhalations recorded by the incoming audio data 302.

In some examples of FIG. 3, the classification algorithm 304 may be utilized to process the incoming audio data 302. For instance, the classification algorithm 304 can be configured to utilize digital signal processing tools such as a Fast Fourier Transformation (FFT) filter, audio signal filters, spectrum analysis tools, and other signal processing tools. For example, the incoming audio data 302 can be passed through a FFT filter configured to break the incoming audio data 302 into frequency-amplitude components that are associated with pitch-amplitude and/or pitch volume. Additionally, rhythm of an audio feature can be represented by the pattern of sounds produced. For instance, the rhythm of the audio feature can be determined by extracting compressions/peaks and rarefaction/troughs from the waveform of the audio data and comparing/analyzing the compressions/peaks and the rarefaction/troughs of the audio data. Further, the classification algorithm 304 can extract the average duration of compression vs. rarefaction associated with the audio sample for classification of the audio sample. In an additional example, the tone of the audio sample may be determined based on one or more specified frequencies of the audio waveform that are associated with an extremely high amplitude relative to the other frequencies of the audio waveform. When subjected to FFT analysis, the breakdown of the audio data into frequency and amplitude components can be utilized to determine the tone associated with the audio data. In a further example, the classification algorithm can utilize techniques such as Linear Predictive Codes (LPC), Perceptual Linear Prediction (PLP), Mel Frequency Cepsral Coefficients (MFCC), and other techniques to extract audio features from the recorded audio samples. For instance, MFCCs may be determined based on the shape of the vocal tract of the patient and may be utilized as an identifier of the patient based on the voice produced by the shape of the vocal track represented by the MFCCs. Additionally, the MFCCs can be determined based on audio data being broken into overlapping frames and apply a series of FFTs and filters to the audio data to extract/identify the MFCCs for the audio data and for the patient. Accordingly, the LPCs, the PLPs, and the MFCCs may be utilized as indicators to classify the audio sample associated with the patient. Further, variations in the LPCs, the PLPs, and the MFCCs may further be classified as and/or associated with one or more symptoms/respiratory conditions. The audio data may include the audio energy, the audio spectrum, the audio amplitude, the audio intensity, and/or the MFCC (and/or other indicators) may be utilized to identify features for extraction and classification by the classification algorithm 304. Accordingly, the various indicators identified above may be tracked and utilized to identify whether a segment of the audio data is to be classified as vocal utterance data 306 or breathing data 308.

In some examples of FIG. 3, the vocal utterance data 306 may be further analyzed by a voice recognition algorithm 310 after classification by the classification algorithm 304. For example, the voice recognition algorithm 310 may be configured identify vocal/vocal characteristics 316 of the patient within the vocal utterances 306. Similar to the classification algorithm, the voice recognition algorithm 310 may have access to a database containing a plurality of voice samples associated with the patient. Additionally, the voice recognition algorithm 310 may utilize machine learning algorithms and neural networks trained based on the plurality of patient voice samples to identify portions of the vocal utterances that are associated with the patient. Further, the voice recognition algorithm may be configured to identify vocal characteristics 316 that can include pitch, tone, rhythm, volume, and rate of speech associated with the patient. It should be noted that the machine learning algorithms and neural networks can be trained to also identify a deviation in vocal characteristics 316 from stored patient vocal characteristics and/or identify stored patient vocal characteristics that match the identified vocal characteristics 316.

In some examples of FIG. 3, the vocal utterance data 306 may be further analyzed by the audio event recognition algorithm 312 after classification by the classification algorithm 304. For example, the audio event recognition algorithm 312 may be configured identify audio events 318 associated with the patient within the vocal utterances 306. Similar to the classification algorithm, the audio event recognition algorithm 312 may have access to a database containing a plurality of past audio events associated with the patient. As noted above, audio events can include groans, whines, wheezes, moans, coughs, and other utterances that are not associated with speech, but indicate a status of airways of the patient. Additionally, the audio event recognition algorithm 312 may utilize machine learning algorithms and neural networks trained based on the plurality of past audio event samples to identify portions of the vocal utterances that are audio events produced by the patient. Accordingly, the audio event recognition algorithm 312 may identify audio events 318 from the vocal utterances 306.

In some examples of FIG. 3, the breathing data 308 identified by the classification algorithm may be further analyzed by a breath pattern analysis algorithm 314. For example, the breathing data 308 may comprise repeated inhalation and exhalation, by the patient, during speech, rest, and activity. Additionally, the breathing pattern analysis algorithm 314 may be configured to track the duration, rate, effort, and other breath characteristics 320 associated with the breathing data 308. Further, the breathing pattern analysis algorithm 314 may be configured to identify breath patterns that are indicative of the health status of the patient. For instance, and similar to above, the breathing pattern analysis algorithm 314 may utilize machine learning techniques and/or neural networks to identify breath characteristics 320 and/or relevant breathing patterns from the incoming audio data 302. The breathing pattern analysis algorithm 314 may have access to database comprised of breathing patterns associated with respiratory illnesses and/or respiratory conditions (e.g., recordings of individuals and/or the patient undergoing an asthma episode, coughing due to illness, etc.), recordings indicative of previous breathing characteristics associated with the patient, and other recording associated with the breathing patterns of the patient.

Figure 4:
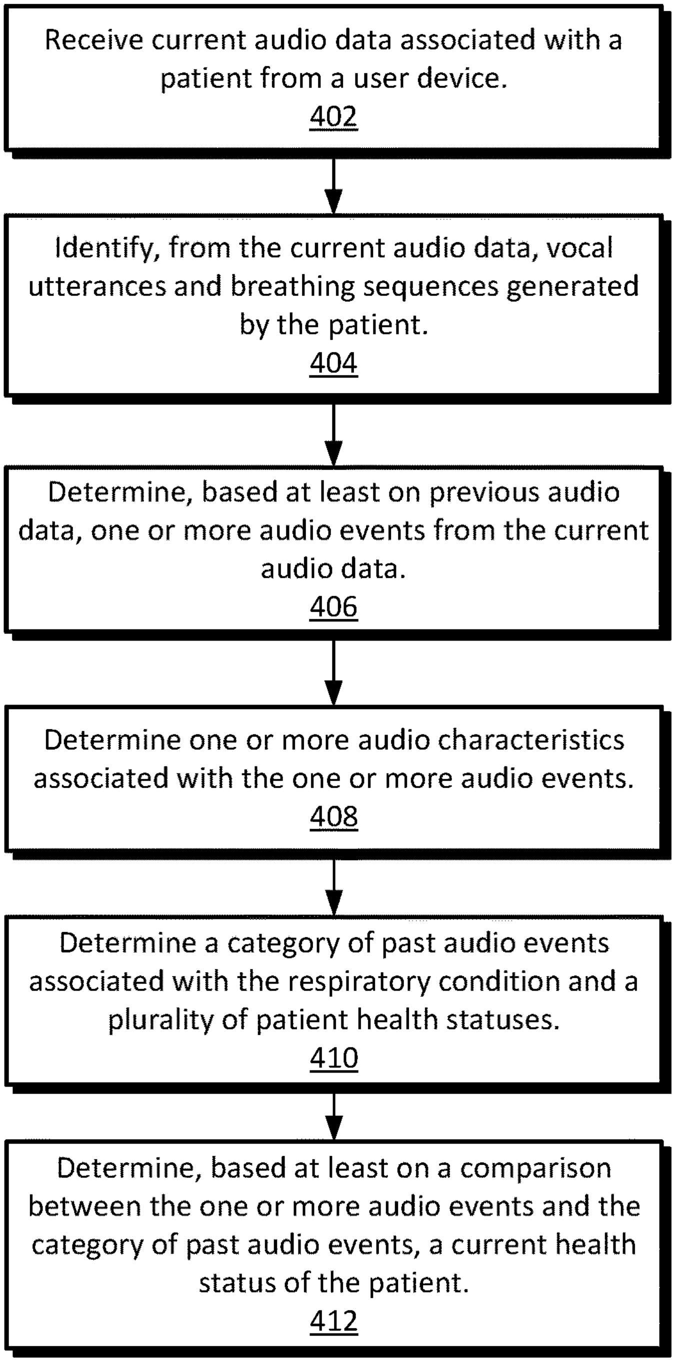
FIG. 4 provides a flow diagram illustrating an example method of the present disclosure.

FIG. 4 provides a flow diagram illustrating an example method 400 for monitoring a health status of a patient. The method 400 is illustrated as collections of blocks in a logical flow graph, which represents a sequence of operations that can be implemented in hardware, software, or a combination thereof. In the context of software, the blocks represent computer-executable instructions stored on one or more computer-readable storage media that, when executed by computer processing unit(s) (CPU(s)), perform the recited operations. Generally, computer-executable instructions include routines, programs, objects, components, data structures, and the like that perform particular functions or implement particular abstract data types. The order in which the operations are described is not intended to be construed as a limitation, and any number of the described blocks can be combined in any order and/or in parallel to implement the method 400. In some embodiments, one or more blocks of the method 400 can be omitted entirely.

At block 402, the CPU of a patient monitoring system may receive current audio data associated with a patient that has a respiratory condition from a user device. As has been described above the user device may be a medical device, a personal device, an assistant device, or other device associated with a patient monitoring system. In some example methods, the various devices associated with the patient monitoring system may be further associated with a microphone and may be configured to transmit the current audio data to the patient monitoring system via a communication network. The current audio data may be transmitted by the devices, to the patient monitoring system, on a substantially periodic, aperiodic, or continuous basis. Transmission on a periodic basis may comprise transmitting the current audio data to the patient monitoring system on a substantially regular interval (e.g., after a number of seconds, minutes, hours, days, etc. has passed since the previous transmission of the current audio data). Transmission on an aperiodic basis may comprise transmitting the current audio data when one or more audio data thresholds are satisfied, when information transmission is requested, or at other instances that may not occur on a substantially regular basis. Transmission on a continuous basis may comprise transmitting the current audio data at substantially the same time that the current audio data was captured/recorded by the user device.

At block 402, and in some additional examples, the current audio data may be collected during a medical treatment for the respiratory condition of the patient or in a non-medical environment associated with the patient. For instance, the current audio data may be captured by a microphone associated with a medical device while the patient is receiving medical treatment, advice, and/or consultation from a medical practitioner. Alternatively, or in addition, the current audio data may be captured by a microphone associated with a personal device of the patient while the patient is at home, in public, and/or otherwise completing daily activities (e.g., conversing, eating, sleeping, etc.).

At block 404, the CPU of the patient monitoring system may parse the current audio data to identify vocal utterances and/or breathing sequences associated with the patient. As noted with respect to FIG. 3, the patient monitoring system may utilize various algorithms (e.g., voice recognition, machine learning, neural networks, etc.) to identify portions of interest within the current audio data. It should be noted that parsing the current audio data to identify the vocal utterances and the breathing sequences may include the CPU executing a classification algorithm configured to distinguish the vocal utterances and the breathing sequences produced by the patient within the current audio data from background audio of the current audio data. Additionally, identifying the portions of interest (e.g., the vocal utterances, breathing sequences, and/or other sounds generated by the patient) from the current audio data may include the patient monitoring system calling algorithms trained to recognize spoken language and other noises produced by the patient within excess audio data (e.g., other individuals speaking and breathing) and ambient noise (e.g., objects moving, devices outputting audio content, mechanical noises, etc.) within the current audio data. Further, the CPU of the patient monitoring system may execute operations from various algorithms and methods described with respect to FIGS. 1-3 while identifying the vocal utterances and the breathing sequences of the patient.

In some embodiments of block 404, the algorithms may utilize machine learning techniques to identify portions of the audio data as indicators of a current patient health status. In particular, the machine learning algorithm can be trained based on a set of audio data features extracted from a plurality of audio samples stored by a database. The set of audio data features can be utilized to determine a health status of the patient based on a comparison between the current audio features and the set of audio features associated with past patient audio data and past patient health statuses. For instance, machine learning algorithm may determine a current health status of the patient from current audio samples matching one or more audio features associated with past audio data and a past health status of the patient. Additionally, the set of audio data features can include the pitch of the voiced segments, the audio data amplitude, the audio energy, and other audio characteristics associated with the past audio data. Alternatively, or in addition, the set of features can be associated with MFCCs associated with the shape of the vocal cord tract during generation of the set of audio data features of the past audio data. Accordingly, the machine learning algorithm can determine a current health status of the patient based on current audio features matching one or more audio features from the set of audio features. For instance, the machine learning algorithm may compare audio characteristics/MFCCs of the current audio data with the past audio characteristics/past MFCCs associated with the set of audio features. Further, the machine learning algorithm may return the one or more past audio features and past health statuses associated with the one or more past audio features. From the past health statuses, the machine learning algorithm can be configured to identify the current health status based on a closest match between the one or more past audio features and the current audio feature. Similarly, normalized audio pitch, amplitude, energy, intensity, and MFCC from past audio samples can be utilized to train a classifier configured to predict a closest match between the past audio samples and the current audio samples.

At block 406, the CPU of the patient monitoring system may determine one or more audio events from the vocal utterances and/or the breathing sequences based at least on previous vocal utterances and previous breathing sequences associated with the patient. In some examples, the vocal utterances may include one or more audio events comprising a conversation, a requested phrase, an audible pain event, and/or an exclamation associated with the patient. Alternatively, or in addition, the breathing sequences may include one or more additional audio events are determined comprising an inhalation, an exhalation, a cough, a sneeze, and/or a strained breath associated with the patient. Further, the one or more audio events may include additional audible sounds produced by the patient including gasps, wheezes, whines, cries, and other sounds associated with difficulty breathing, pain, and the respiratory condition/illness of the patient.

At block 408, the CPU of the patient monitoring system may determine one or more audio characteristics associated with the one or more audio events. As described above by FIGS. 1-3, the one or more audio characteristics may comprise, a pitch of the vocal utterances, a tone of the vocal utterances, a rhythm of the vocal utterances, a volume of the vocal utterances, a rate of speech associated with the vocal utterances, an inhalation duration associated with the breathing sequences, an exhalation duration associated with the breathing sequences, and/or a rate of breathing associated with the breathing sequences. Additionally, in some examples, the audio characteristics may include additional audio characteristics associated with strained speaking and breathing, painful speaking and breathing, labored speaking and breathing, and/or other human audible/human inaudible audio characteristics associated with the health status of the patient. Further, the various audio characteristics may be identified by a voice recognition algorithm configured to break human speech/sounds into constituent components, parts, and/or variables. The various aspects that comprise human speech may be determined based on analysis of a spectrogram (e.g., a visual representation of recorded audio data) and/or other electronic data formats associated with the current audio data.

At block 410, the CPU of the patient monitoring system may determine a category of past audio events associated with the one or more audio events based at least on the one or more audio characteristics. Additionally, the category of past audio events may include a set of past audio recordings associated with the respiratory condition and a plurality of patient health statuses. In some examples, the category of past audio events can be comprised of a plurality of recorded audio events associated with a vocal utterance type and/or a breathing sequence type. It should be noted that the vocal utterance type and/or the breathing sequence type may be characterized by at least a set of audio characteristics selected from the various audio characteristics described above. For example, the category of past audio events may be associated with exclamations, which would be associated with a set of various audio characteristics associated with the vocal utterances that comprise the exclamation category. Additionally, a category for the one or more audio events of may be determined based at least on the one or more audio characteristics, including at least the set of audio characteristics. For instance, where the one or more audio characteristics associated with the one or more audio events match the set of audio characteristics associated with the exclamation category, the one or more audio events may be determined to include one or more exclamations. Further, particular audio events of the one or more audio events may be flagged as exclamations due to their association with the set of audio characteristics.

At block 412, the CPU of the patient monitoring system may determine a current health status of the patient associated with the respiratory condition based at least on a comparison between the one or more audio events and the category of past audio events. In some examples, determining the current health status of the patient may further comprise determining one or more recorded health statuses associated with the respiratory condition of the patient and determining the current health status associated with the respiratory condition of the patient. As noted above, the category of past audio events may comprise a plurality of recorded audio events associated with a vocal utterance type and/or a breathing sequence type. The plurality of recorded audio events can be previously analyzed to identify the one or more recorded health statuses that are associated with the audio characteristics of the plurality of recorded audio events. Accordingly, the CPU of the patient monitoring system may utilize the associations between various respiratory symptoms and the one or more recorded health statuses to determine the current health status of the patient based on the current respiratory symptoms associated with the one or more audio events of the current audio data.

At block 412, and in some examples, the CPU of the patient monitoring system may be configured to determine correlations between the one or more audio characteristics associated with one or more audio events of audio data and respiratory symptoms of the patient. For example, the recorded health statuses associated with the category of past audio events may comprise one or more respiratory symptoms associated with the plurality of recorded audio events, the one or more respiratory symptoms including at least one of: inflammation of patient airways, strained inhalation, strained exhalation, excess mucus in the patient airways, chronic cough, one or more modified audio characteristics produced by the patient, bloody cough, shortness of breath, and chest discomfort/pain. Accordingly, the CPU of the patient monitoring system may determine present symptoms for the one or more audio events by identifying correlations between respiratory symptoms of the category of past audio event and the one or more past audio characteristics that may be applied to the one or more audio characteristics. Alternatively, or in addition, the one or more recorded health statuses may include an initial health status associated with initial audio characteristics and initial patient symptoms recorded before a medical treatment of the respiratory condition; a target health status associated with target audio characteristics and target patient symptoms recorded while the respiratory condition was effectively treated or the patient was unassociated with the respiratory condition; and a threshold health status associated with threshold audio characteristics, wherein an indication is transmitted, by the system, to the patient or a medical practitioner based at least on the one or more audio characteristics satisfying the threshold audio characteristics.

Figure 5:
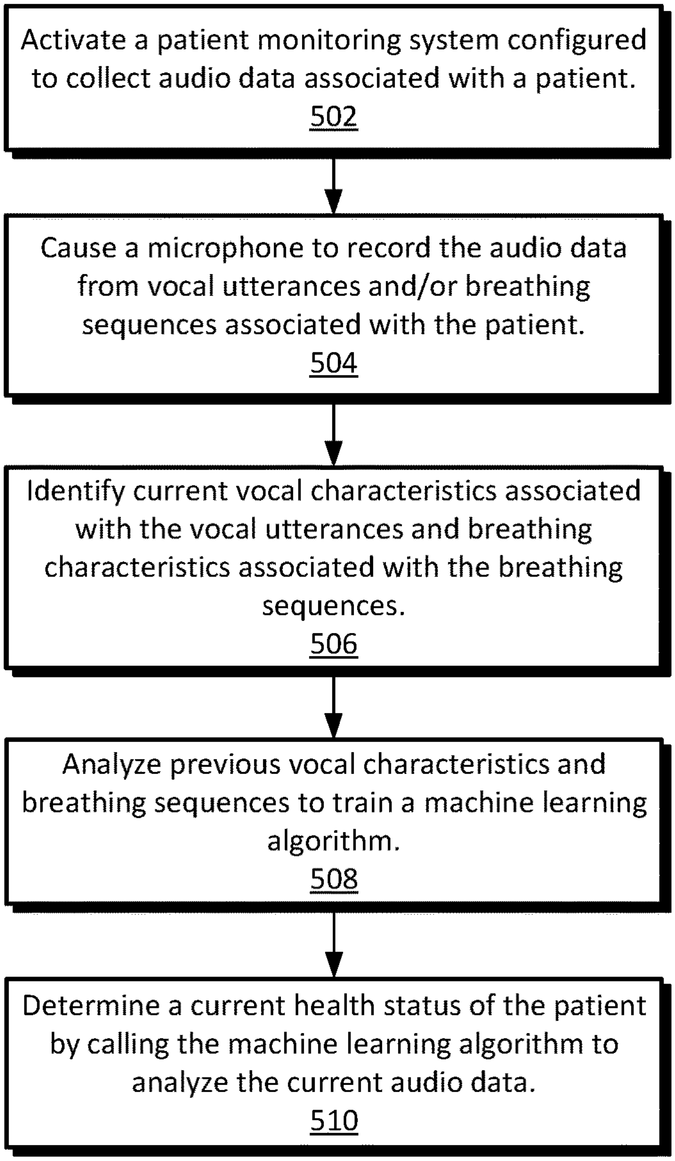
FIG. 5 provides a flow diagram illustrating another example method of the present disclosure.

FIG. 5 provides a flow diagram illustrating an example method 500 for monitoring a health status of a patient, as described herein. The method 500 is illustrated as collections of blocks in a logical flow graph, which represents a sequence of operations that can be implemented in hardware, software, or a combination thereof. In the context of software, the blocks represent computer-executable instructions stored on one or more computer-readable storage media that, when executed by CPU(s), perform the recited operations. Generally, computer-executable instructions include routines, programs, objects, components, data structures, and the like that perform particular functions or implement particular abstract data types. The order in which the operations are described is not intended to be construed as a limitation, and any number of the described blocks can be combined in any order and/or in parallel to implement the method 500. In some embodiments, one or more blocks of the method 500 can be omitted entirely.

AT block 502, the CPU of a patient monitoring system may activate a patient monitor or activate a patient monitoring process, wherein the patient monitor may be a microphone associated with a user device (e.g., a medical device, a personal device, an assistant device, etc.) and configured to collect current audio data associated with respiratory functionality of a patient. The respiratory functionality of the patient may be associated with an ability of the patient to breath, speak, or otherwise utilize patient airways. As noted above, the respiratory functionality of the patient may be compromised by a respiratory condition (e.g., respiratory illness, respiratory disease, respiratory problems, etc.) depending at least in part on the severity of respiratory symptoms experienced by the patient due to the respiratory condition. In some examples, the patient monitoring system may be configured to collect and store audio data from a plurality of patients.

At block 504, the CPU of the patient monitoring system may cause a microphone to record the current audio data from patient vocal utterances and patient breathing sequences. As noted above, the respiratory functionality of a patient may be affected by the severity of respiratory symptoms experienced by the patient due to the respiratory condition(s). Accordingly, causing the microphone to monitor and record the patient speaking (e.g., in conversations, to themselves individually, in response to a prompt, etc.), breathing, or otherwise generating sounds that are audible or inaudible to humans produces the current audio data from the vocal utterances and breathing sequences of the patient.

At block 506, the CPU of the patient monitoring system may identify current vocal characteristics associated with the patient vocal utterances and current breathing characteristics associated with the patient breathing sequences. In some examples, the identification of the current vocal characteristics and the current breathing characteristics may be performed by the CPU in a manner discussed above. In some additional examples, the identification of the current vocal characteristics and the current breathing characteristics may be determined from one or more audio spectrograms. For instance, the CPU may determine a pitch, a tone, a rhythm, a volume, and a rate of speech associated with the patient from one or more audio spectrograms associated with the patient speaking. Additionally, the CPU may determine a breathing rate and an average breath volume from one or more additional spectrograms associated with patient breathing sequences. Further, the CPU may identify one or more pain events from one or more further spectrograms, wherein the one or more pain events are associated with one or more whines, one or more groans, or one or more grunts.

At block 508, the CPU of the patient monitoring system may analyze a plurality of previous vocal characteristics and breathing sequences associated with the patient and the previous audio data to train a machine learning algorithm. For instance, the plurality of previous vocal characteristics and breathing sequences may include previous patient vocal characteristics, previous patient breathing sequences, vocal characteristics associated with one or more additional patients, and breathing sequences associated with the one or more additional patients. The previous vocal characteristics and breathing sequences may comprise spectrograms or other recordings of audio data that reflect the ability of the patient or the one or more additional patients to speak and breathe while experiencing a set of respiratory symptoms. Accordingly, each set of vocal characteristics and breathing sequences may be associated with a patient health status and a set of respiratory symptoms. Further, the set of vocal characteristics and breathing sequences may be further associated with contextual or demographic information to provide more accurate matching of symptoms the patient is experiencing with the set of respiratory symptoms experienced by patients associated with the plurality of previous vocal characteristics and breathing sequences.

At block 508, and in some examples, analyzing the plurality of previous vocal characteristics and breathing sequences to train the machine learning algorithm may comprise training the machine learning algorithm from previously evaluated audio recordings or previously diagnosed audio recordings. For instance, the CPU of the patient monitoring system may receive one or more diagnosed audio recordings, wherein a diagnosed audio recording of the one or more diagnosed audio recordings is associated with a respiratory condition, a recorded health status, and a set of previous vocal characteristics. Additionally, the CPU can provide the machine learning algorithm the recorded health status and the set of previous vocal characteristics of individual diagnosed audio recordings of the one or more diagnosed health recordings. Further, the CPU may call the machine learning algorithm to correlate the plurality of previous vocal characteristics and breathing sequences based at least on the recorded health status and the set of previous vocal characteristics for each individual diagnosed health recording of the one or more diagnosed audio recordings. In general, the one or more diagnosed audio recordings may comprise recordings of vocal utterances and/or breathing sequences recorded from the patient and/or one or more additional patients, wherein the one or more additional patients may share respiratory symptoms, demographic information, contextual information, and/or other associations with the patient. The one or more diagnosed audio recordings may be previously evaluated, graded, and/or diagnosed and associated with one or more respiratory conditions, one or more respiratory symptoms, a severity of the respiratory condition(s)/symptoms(s), and other information associated with the recorded health status of the source (e.g., the patient and/or the one or more additional patients) of the diagnosed audio recording. Accordingly, the machine learning algorithm can receive digital information regarding the one or more diagnosed audio recordings and generate correlations between the audio characteristics of the diagnosed audio recordings and the symptoms of the sources of the diagnosed audio recordings.

At block 510, the CPU of the patient monitoring system may determine, through utilization of the machine learning algorithm, a current health status associated with the patient. For instance, the current health status of the patient may be determined from a comparison of the current vocal characteristics with the plurality of previous vocal characteristics. In some examples, determining the current health status associated with the patient may utilize a trained machine learning algorithm to determine the current health status based on one or more health statuses associated with the one or more diagnosed audio recordings. For example, the CPU may compare the current vocal characteristics of the patient with the plurality of previous vocal characteristics and breathing sequences. Additionally, the CPU may identify the diagnosed audio recording associated with the set of previous vocal characteristics determined to substantially match the current vocal characteristics. The set of previous vocal characteristics may be determined to substantially match the current vocal characteristics based on an analysis of the respective spectrograms associated with the diagnosed audio recording(s) and the current audio data. Alternatively, or in addition, the CPU may utilize the correlations between recorded patient health statuses/symptoms and the one or more diagnosed audio recordings to determine a severity associated with the symptoms indicated by the current audio data. In other words, the one or more diagnosed audio recordings may indicate a spectrum of changes to the vocal characteristics of a data source (e.g., the patient and/or the one or more additional patients) that are caused by various sets of respiratory symptoms associated with different severities. Accordingly, the CPU may determine, based at least on the recorded health status (e.g., recorded respiratory symptom severity), the current health status of the patient.

Figure 6:
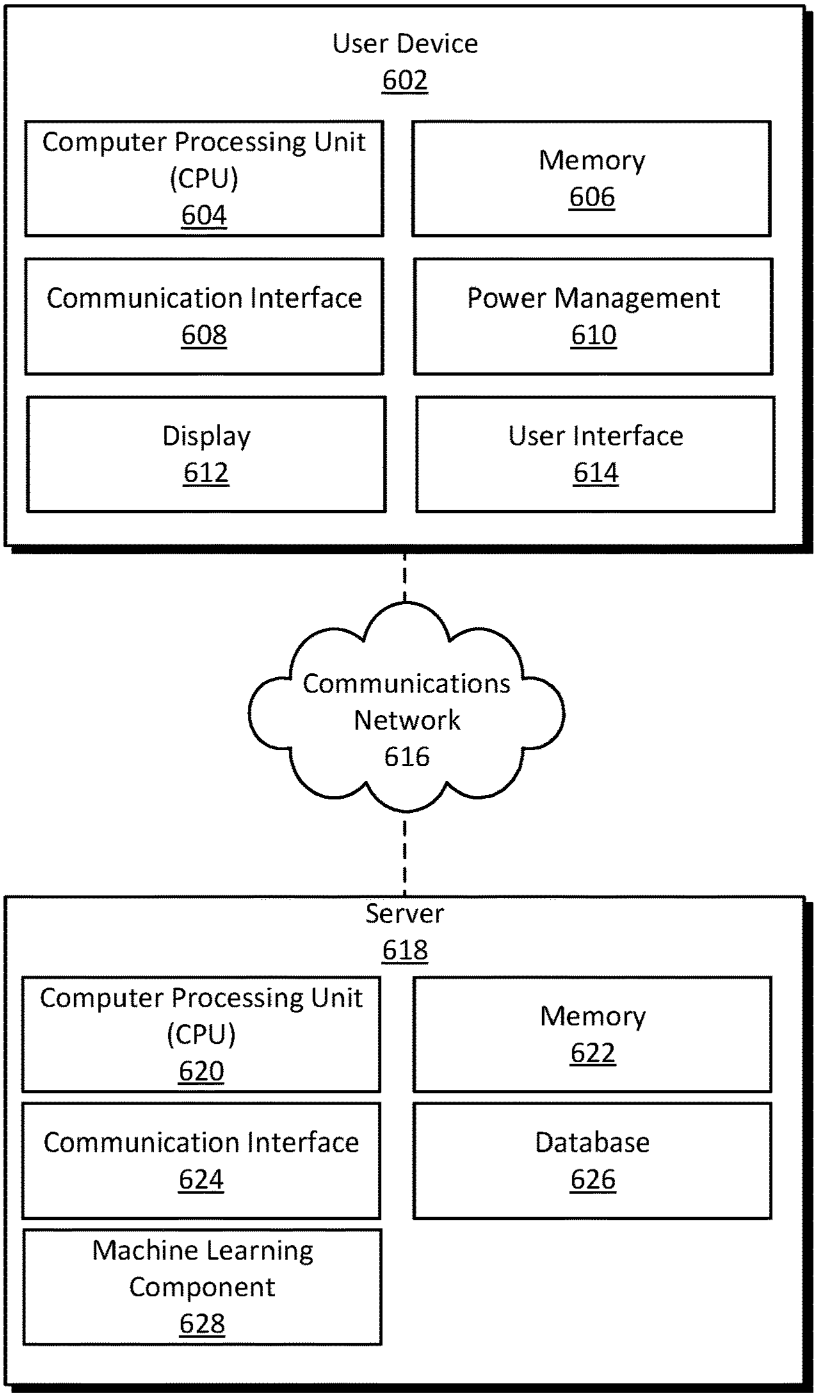
FIG. 6 provides an example user device and server of the present disclosure that may operate to monitor a current health status of a patient.

FIG. 6 illustrates an example patient monitoring system, as described herein. The patient monitoring system may utilize a user device 602 in communication, via communication network 616, with a server 618. In particular, the user device 602 may comprise a computer processing unit (CPU) 604, memory 606, a communication interface 608, a power management component 610, a display 612, and a user interface 614. Additionally, the server 618 may computer a CPU 620, memory 622, a communications interface 624, a database 626, a machine learning component 628, and a neural network component 630.

In some examples of FIG. 6, the CPU 604 and the CPU 620 may be configured to perform or partially perform methods described by FIGS. 1-5. Additionally, or alternatively, the CPU 604 may operate to control a microphone associated with the user device to capture audio data related to the patient. The CPU 604 may communicate with the CPU 320, and the CPU 620 may communicate with the CPU 604, via the communication interface 608 and the communication interface 624 to receive indications of routines and/or algorithms to be performed and to transmit the captured audio data during the routines and/or algorithms.

In the example shown in FIG. 6, the CPU 604 of the user device 602 may comprise one or more controllers, processors, and/or other hardware and/or software components configured to operably a microphone associated with the user device 602, the communication interface 608, the power management component 610, the display 612, the user interface 614, and other components of the user device 602. For instance, the CPU 604 shown in FIG. 6 may include a single processing unit (e.g., a single processor) or a number of processing units (e.g., multiple processors), and can include single or multiple computing units or multiple processing cores. The CPU 602 shown in FIG. 6 can be implemented as one or more microprocessors, microcomputers, microcontrollers, digital signal processors, central processing units, state machines, logic circuitries, and/or any devices that manipulate signals based on operational instructions. For example, CPU 602 shown in FIG. 6 can be one or more hardware processors and/or logic circuits of any suitable type specifically programmed or configured to execute the algorithms, operations, and methods described above and herein. The CPU 602 shown in FIG. 6 can be configured to fetch and execute computer-readable instructions stored in memory 606, which can program the CPU 602 to perform the functions described here. Additionally, or alternatively, the CPU 602 shown in FIG. 6 can be configured to fetch and execute computer-readable instructions stored in audio screening components 126 of the audio analysis system 120 (FIG. 1).

In some respects, the memory 606 shown in FIG. 6 may be similar to the audio screening components 126 described above with respect to the audio analysis system 120 (FIG. 1). For example, the memory 606 may include volatile and nonvolatile memory and/or removable and non-removable media implemented in any type of technology for storage of information, such as computer-readable instructions, data structures, program modules, or other data. Such memory 606 can include, but is not limited to, RAM, ROM, EEPROM, flash memory or other memory technology, optical storage, solid state storage, magnetic tape, magnetic disk storage, RAID storage systems, storage arrays, network attached storage, storage area networks, cloud storage, or any other medium that can be used to store the desired information and that can be accessed by a computing device. The memory 606 can be a type of computer-readable storage media and/or can be a tangible non-transitory media to the extent that when mentioned, non-transitory computer-readable media exclude media such as energy, carrier signals, electromagnetic waves, and signals per se.

The memory 606 can be used to store any number of functional components that are executable and the audio data to be processed by CPU 604 and/or transmitted via the communication interface 608. In many implementations, these functional components comprise instructions or programs that are executable by the CPU(s) 602 and that, when executed, specifically configure the one or more CPU (s) 602 to perform the actions described herein and associated with monitoring the current health status of the patient.

Other functional components stored in the memory 606 may include, among other things, a graphical representation data component, a measurement data component, a threshold data component, a notification component, a microphone data component, a machine learning component, a neural network component, and/or any other functional component associated with the operation of the patient monitoring system.

In some examples, the communication interface 608 shown in FIG. 6 may be configured to transmit information via the communications network 616 to the communications interface 624. For instance, the communication interface 608 and the communication information 624 may enable the user device 602 and the server 618 to exchange indications of audio data, patient health status, indications of audio data to be collected, and/or other information using wired or wireless connections. Wireless connections can include cellular network connections and connections made using protocols such as 802.11a, b, g, and/or ac. In other examples, a wireless connection can be accomplished between the audio user device and the server using one or more wired or wireless protocols, such as Bluetooth, Wi-Fi Direct, radio-frequency identification (RFID), infrared signals, and/or Zigbee. Other configurations are possible. Similarly, the communication network 616 is typically any type of wireless network or other communication network known in the art. Examples of network 616 include the Internet, an intranet, a wide area network (WAN), a local area network (LAN), and a virtual private network (VPN), cellular network connections and connections made using protocols such as 802.11a, b, g, n and/or ac.

In any of the examples described herein, the CPU 602 shown in FIG. 6 may be configured to receive various information, signals, and/or other inputs from the microphone associated with the user device 602, the display 612, the user interface 614 and/or other components of the user device 602. In some examples, the user interface 614 may receive such inputs from a user, a patient, and/or a medical practitioner, and one or more such inputs may comprise a command or a request for the patient monitoring system to generate, display, provide, and/or otherwise output one or more patient health statuses, audio data, patient symptom reports, and/or other output generated during monitoring of the patient. In some additional examples, the display 612 may comprise, for example, a liquid crystal display (LCD), a light emitting diode (LED) display, an organic light emitting diode (OLED) display, or active matrix organic light emitting display (AMOLED). Additionally, the display 612 may be an interactive display that is configured to receive touch input for the user interface 614. Alternatively, or in addition, the user interface 614 may receive user input via keyboard, mouse, or other input device.

In the example shown in FIG. 6, the CPU 620 of the server 618 may comprise one or more controllers, processors, and/or other hardware and/or software components configured to operably a microphone associated with the server 618, the communication interface 624, the database 626, the machine learning component 628, the neural network component, and other components of server 618. For instance, the CPU 620 shown in FIG. 6 may be substantially similar to the CPU 602. Additionally, the memory 622 may be comprise of computer-executable instructions similar to the memory 606 of the user device 602. Further, the database 626 may be configured as described above with respect to FIGS. 1-5.

In the example shown in FIG. 6, the machine learning component 628 may be configured as discussed above with respect to FIGS. 1-5. In general, the machine learning component 628 represents a series of instruction for causing the processor to process a training set of data to establish correlations between audio characteristics of the incoming audio data and previously recorded patient symptoms associated with various respiratory conditions based on the recorded audio characteristics for the recorded patient symptoms. The larger the training data set, the more accurate the determination regarding the current health status of the patient based on the previously recorded patient symptoms and recorded audio characteristics will generally be. Accordingly, the machine learning component may provide an algorithm capable of monitoring the incoming audio data from the patient and tracking the current health status based on previously analyzed and characterized audio data for the patient and/or other patients that share similar categorization information. In some additional examples, the machine learning component 628 may include algorithms that utilize neural networks to categorize incoming audio data from the patient and determine a current health status for the patient based on the audio characteristics of the incoming audio data. For instance, a neural network may be developed from a training data set that establishes branching categories of audio data characteristics that are associated with individual respiratory symptoms, respiratory conditions, and types of sounds produced by the patient.

It should be noted that while the above discussion primarily relates to the analysis of audio data related with a user speaking, breathing, and/or otherwise generating utterances via the airways and vocal cords of the patient, other sounds may be analyzed by the system. For example, footsteps of the patient may be tracked by a microphone to identify changes in gait that may be caused by pain, lack of breath, and other issues. Alternatively, or in addition, the audio characteristics of the vocal utterances produced by the patient may be able to indicate potential health issues beyond respiratory conditions. Further, other aspects of the current health status associated with the patient may be tracked via audio characteristics. For example, by tracking different breathing modes of the patient, a model of the sleeping habits may be tracked and significant events or changes in the breathing patterns during sleep may be utilized to indicate the current health status of the patient. Accordingly, this disclosure is not limited to the explicitly disclosed methods, systems, and apparatuses, but is intended to include variations to and modifications thereof, which are within the spirit of the following claims.

The foregoing is merely illustrative of the principles of this disclosure and various modifications can be made by those skilled in the art without departing from the scope of this disclosure. The above described examples are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

As a further example, variations of apparatus or process limitations (e.g., dimensions, configurations, components, process step order, etc.) can be made to further optimize the provided structures, devices and methods, as shown and described herein. In any event, the structures and devices, as well as the associated methods, described herein have many applications. Therefore, the disclosed subject matter should not be limited to any single example described herein, but rather should be construed in breadth and scope in accordance with the appended claims.

What is claimed is:

1. A system, comprising:

memory;

one or more processors;

an audio sensor operably connected to the one or more processors; and computer-executable instructions stored in the memory and executable by the one or more processors to perform operations comprising:

receiving current audio data associated with a patient, the current audio data being collected during a lung health evaluation of the patient via the audio sensor;

identifying, using a voice recognition component stored in the memory and based at least on the current audio data, at least one of a vocal utterance or a breathing sequence of the patient;

determining, based on the at least one of the vocal utterance or the breathing sequence, and on at least one of previous vocal utterances associated with the patient or previous breathing sequences associated with the patient, one or more audio events;

determining a first audio characteristic associated with the one or more audio events;

determining, based at least on the first audio characteristic, a category of audio events associated with the one or more audio events, wherein the category of audio events is further associated with a second audio characteristic indicative of a respiratory condition of the patient;

retrieving, from a database, diagnostic data including respective audio data and a corresponding health status associated with a plurality of other patients;

determining, based on the diagnostic data, a subset of the plurality of other patients, wherein the subset includes patients exhibiting an audio event matching the one or more audio events;

determining, by a patient status component, using the corresponding health status included in the diagnostic data associated with the subset, a current health status of the patient;

generating, based at least in part on the current health status, a message comprising the current health status, a severity of the respiratory condition, and a recommendation associated with care of the patient; and causing the message to be displayed via a user interface of a device associated with a medical provider.

2. The system of claim 1, wherein the audio sensor is configured to:

attach to a vest adapted to be worn by the patient, and transmit the current audio data to the one or more processors on a substantially periodic, aperiodic, or continuous basis.

3. The system of claim 1, wherein:

the current audio data is collected from the patient after a treatment or a diagnosis associated with the respiratory condition; and the current health status of the patient is tracked to monitor a recovery from the respiratory condition.

4. The system of claim 1, wherein the one or more audio events:

are determined based at least in part on the vocal utterance, and comprise at least one of a requested phrase, an audible pain event, or an exclamation associated with the patient.

5. The system of claim 1, wherein the one or more audio events are determined based at least in part on the breathing sequence, the one or more audio events comprising at least one of an inhalation, an exhalation, a cough, a sneeze, or a strained breath associated with the patient.

6. The system of claim 1, wherein the first audio characteristic comprises at least one of:

a tone of the vocal utterance;

a rhythm of the vocal utterance;

a volume of the vocal utterance; or a rate of speech associated with the vocal utterance.

7. The system of claim 1, wherein:

the category of audio events is comprised of recorded audio events associated with a vocal utterance type or a breathing sequence type, the vocal utterance type or the breathing sequence type characterized at least by the second audio characteristic; and the category of audio events is determined based at least on the first audio characteristic including at least the second audio characteristic.

8. The system of claim 1, wherein the diagnostic data includes one or more respiratory symptoms associated with the plurality of other patients, the one or more respiratory symptoms including at least one of:

inflammation of patient airways;

strained inhalation;

strained exhalation;

excess mucus in the patient airways;

chronic cough;

one or more modified audio characteristics;

bloody cough;

shortness of breath; or chest discomfort.

9. The system of claim 1, wherein the corresponding health status comprises:

an initial health status associated with initial audio data and initial patient symptoms recorded before a medical treatment of the respiratory condition;

a target health status associated with target audio data and target patient symptoms; or an actual health status associated with actual audio data and actual patient symptoms recorded while the respiratory condition was being treated.

10. The system of claim 1, wherein determining the category of audio events comprises:

accessing a standard audio profile of an audio event; and comparing characteristics of the audio event to the standard audio profile, the characteristics comprising frequency, amplitude, duration, and phase, wherein the category is determined based at least in part on the comparing.

11. The system of claim 1, wherein the recommendation comprises an indication of one or more of additional monitoring of the patient, a diagnosis, assistance from a care provider, reduced monitoring of the patient, an improved health status, or a progressing health status.

12. The system of claim 1, wherein the category of audio events is comprised of recorded audio events, the operations further comprising:

determining an association between a health status of the patient and one or more respiratory symptoms associated with one or more vocal characteristics identified based on the recorded audio events, wherein the association comprises one or more of an association between:

asthma and inflammation of patient airways;

COPD and an inability to exhale fully or normally;

bronchitis and excess mucus in patient airways;

emphysema and difficulty exhaling air;

lung cancer and one or more of chronic coughing, changes in patient vocal characteristics, harsh breathing sounds, and coughing up blood;

cystic fibrosis and one or more of chronic coughing, frequent lung infections, mucus pooling in patient airways, frequent respiratory infections, wheezing, and shortness of breath;

pneumonia and shortness of breath; or pleural effusions and one or more of chest discomfort and shortness of breath.

13. The system of claim 1, wherein the subset of the plurality of other patients is determined based on matching demographic information associated with the patient with respective demographic information included in the diagnostic data.

14. A system, comprising:

one or more processors;

an audio sensor operably connected to the one or more processors;

memory; and computer-executable instructions stored in the memory and executable by the one or more processors to perform operations comprising:

causing the audio sensor to collect a first audio recording at a first time, wherein the first audio recording includes at least one of a patient speaking or breathing during a lung health evaluation of the patient;

receiving the first audio recording;

determining, based at least on the first audio recording, an audio category associated with a vocal utterance of the first audio recording characterized by a first audio characteristic;

retrieving, from a database, diagnostic data including respective audio data and a corresponding health status associated with a plurality of other patients;

determining, based on the diagnostic data, a subset of the plurality of other patients, wherein the first audio characteristic matches a characteristic of the respective audio data of the subset;

determining, by a patient status component, using the corresponding health status included in the diagnostic data associated with the subset, a first patient health status associated with the patient;

causing the audio sensor to collect a second audio recording at a second time, after the first time;

determining, based at least on the second audio recording, a second audio characteristic associated with the second audio recording;

determining, by the patient status component, based at least on comparing the first audio characteristic with the second audio characteristic, a second patient health status, wherein the second patient health status indicates a change in health status relative to the first patient health status;

generating, based at least in part on the change in health status, a message comprising the first patient health status and the second patient health status, and a recommendation associated with care of the patient; and causing the message to be displayed via a user interface of a device associated with a medical provider.

15. The system of claim 14, wherein determining the audio category associated with the first audio recording further comprises causing a machine learning algorithm to identify a type of vocal utterance associated with the first audio recording, wherein the type of vocal utterance identifies at least one of a source, a demographic, or a content associated with the vocal utterance.

16. The system of claim 14, the operations further comprising:

determining, based at least on a health status threshold, that the second patient health status satisfies the health status threshold, the health status threshold associated with an increase of respiratory symptoms compared to the first patient health status; and transmitting, from the system to the device associated with the medical provider or a personal device of the patient, an indication of the second patient health status.

17. A non-transitory computer-readable media storing instructions that, when executed by a processor, causes the processor to perform operations comprising:

receiving, from a user device, current audio data collected during a lung health evaluation of a patient, the current audio data being collected via a microphone operably connected to the user device;

identifying, based on the current audio data, at least one of a vocal utterance or a breathing sequence;

determining, based on the at least one of the vocal utterance or the breathing sequence, and on information indicative of at least one of previous vocal utterances or previous breathing sequences, a particular audio event;

determining a first audio characteristic associated with the particular audio event;

determining, based on the first audio characteristic, a category of audio events associated with the particular audio event, wherein the category of audio events is further associated with a second audio characteristic indicative of a respiratory condition;

retrieving, from a database, diagnostic data including respective audio data and a corresponding health status associated with a plurality of other patients;

determining, based on the diagnostic data, a subset of the plurality of other patients, wherein the subset includes patients exhibiting an audio event matching the particular audio event;

determining, using the corresponding health status included in the diagnostic data associated with the subset, a current health status of the patient;

generating, based on the current health status, a message comprising the current health status and a recommendation associated with care of the patient; and providing, based at least on the current health status not satisfying a health status threshold, the message to a device associated with a medical provider.

18. The non-transitory computer-readable media of claim 17, wherein the user device is configured to transmit the current audio data to the non-transitory computer-readable media on a substantially periodic, aperiodic, or continuous basis.

19. The non-transitory computer-readable media of claim 17, wherein:

the current audio data is collected from the patient after a treatment or a diagnosis associated with the respiratory condition; and the current health status is tracked to monitor a recovery from the respiratory condition.

20. The non-transitory computer-readable media of claim 17, wherein the current health status of the patient is determined based on matching respective demographic information and contextual information of the subset with corresponding information associated with the patient.

* * * * *